United States Patent
Elsberg et al.

(10) Patent No.: US 6,524,293 B1
(45) Date of Patent: *Feb. 25, 2003

(54) PREFASTENED DISPOSABLE ABSORBENT ARTICLES HAVING A STRETCH PANEL

(75) Inventors: Laura Linda Elsberg, Woodstock, GA (US); Brian Walter Angielski, Neenah, WI (US); June Marie De Valk, Appleton, WI (US); Tim Joseph Janssen, Kaukauna, WI (US); Patrick Sean McNichols, Hortonville, WI (US); Jennifer Elizabeth Pozniak, Appleton, WI (US); Bruce Reed Shafer, Green Bay, WI (US); James Bennington Stopher, Neenah, WI (US); Gary Lee Travis, Oshkosh, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/466,490

(22) Filed: Dec. 17, 1999

(51) Int. Cl.$^7$ ............................................. A61F 13/15
(52) U.S. Cl. .......................... 604/385.13; 604/385.3; 604/391; 604/396
(58) Field of Search ................. 604/385.01, 385.03, 604/385.04, 385.05, 385.11, 385.13, 385.23, 385.24, 392, 391, 396, 385.3

(56) References Cited

U.S. PATENT DOCUMENTS

| | | | |
|---|---|---|---|
| 1,079,479 A | 11/1913 | Earnshaw |
| 1,485,001 A | 2/1924 | Wills |
| 1,657,909 A | 1/1928 | Abramovich |
| 1,705,194 A | 3/1929 | Marinsky |
| 1,762,468 A | 6/1930 | Brewer |
| 1,963,334 A | 6/1934 | Neilson |

(List continued on next page.)

FOREIGN PATENT DOCUMENTS

| | | |
|---|---|---|
| AU | 667899 | 4/1996 |
| CA | 2096672 | 11/1993 |
| CA | 2103992 A1 | 2/1994 |
| CA | 2187021 A1 | 10/1995 |

(List continued on next page.)

OTHER PUBLICATIONS

Derwent World Patent Database abstract of FR 2762507 A1: description of RAHALA, "Baby's Disposable Nappy."
Derwent World Patent Database abstract of JP 6–063076 A: Description of Kao Corp. (Kaos), "Throw Away Diaper Or Nappy."

(List continued on next page.)

Primary Examiner—Aaron J. Lewis
Assistant Examiner—Jamisue A Webb
(74) Attorney, Agent, or Firm—Jeffrey B Curtin; Alyssa A Dudkowski; John L. Brodersen

(57) ABSTRACT

A prefastened, refastenable, disposable absorbent article includes an absorbent chassis, at least one stretch panel, and a pair a primary fasteners. The absorbent chassis defines a pair of longitudinally opposed end edges and a pair of laterally opposed side edges. The stretch panel is located in one of the waist regions and defines a waist edge, a pair of laterally opposed outboard edges which are located laterally beyond the side edges of the absorbent chassis, and an inward edge which is located longitudinally inward from the waist edge. The pair of primary fasteners are located on the laterally opposed outboard edges of the stretch panel and are releasably prefastened to an opposite waist region of the absorbent chassis to releasably engage a front waist region to a rear waist region to provide the prefastened disposable absorbent article.

39 Claims, 14 Drawing Sheets

U.S. PATENT DOCUMENTS

| | | |
|---|---|---|
| 2,201,255 A | 5/1940 | Wilson, Jr. |
| 2,242,977 A | 5/1941 | Marcos |
| 2,475,175 A | 7/1949 | Cadous |
| 2,477,914 A | 8/1949 | Webb |
| 2,545,761 A | 3/1951 | Brink |
| 2,570,963 A | 10/1951 | Mesmer |
| 2,630,120 A | 3/1953 | Nielson |
| 2,630,806 A | 3/1953 | Kiscaden |
| 2,743,725 A | 5/1956 | Matthews |
| 2,801,632 A | 8/1957 | Burner et al. |
| 2,808,831 A | 10/1957 | Winslett |
| 2,830,589 A | 4/1958 | Doner |
| 2,833,282 A | 5/1958 | Moore |
| 2,910,982 A | 11/1959 | Woodward |
| 2,931,361 A | 4/1960 | Sostrin |
| 3,039,466 A | 6/1962 | Wilson |
| 3,077,193 A | 2/1963 | Mann |
| 3,610,244 A | 10/1971 | Jones, Jr. |
| 3,638,651 A | 2/1972 | Torr |
| 3,653,381 A | 4/1972 | Warnken |
| 3,825,006 A | 7/1974 | Ralph |
| 3,882,871 A | 5/1975 | Taniguchi |
| 4,024,867 A | 5/1977 | Mesek |
| 4,051,853 A | 10/1977 | Egan, Jr. |
| 4,051,854 A | 10/1977 | Aaron |
| 4,066,081 A | 1/1978 | Schaar |
| 4,074,716 A | 2/1978 | Schaar |
| 4,089,068 A | 5/1978 | Swallow |
| 4,090,516 A | 5/1978 | Schaar |
| 4,205,679 A | 6/1980 | Repke et al. |
| 4,210,143 A | 7/1980 | De Jonckheere |
| 4,315,508 A | 2/1982 | Bolick |
| 4,337,771 A | 7/1982 | Pieniak et al. |
| 4,409,049 A | 10/1983 | Passafiume et al. |
| 4,410,327 A | 10/1983 | Baggaley |
| 4,500,316 A | 2/1985 | Damico |
| 4,515,595 A | 5/1985 | Kievit et al. |
| 4,522,853 A | 6/1985 | Szonn et al. |
| 4,525,407 A | 6/1985 | Ness |
| 4,563,185 A | 1/1986 | Reiter |
| 4,568,341 A | 2/1986 | Mitchell et al. |
| 4,581,772 A | 4/1986 | Smith |
| 4,596,055 A | 6/1986 | Aach et al. |
| 4,598,528 A | 7/1986 | McFarland et al. |
| 4,604,096 A | 8/1986 | Dean et al. |
| 4,610,680 A | 9/1986 | LaFleur |
| 4,610,681 A | 9/1986 | Strohbeen et al. |
| 4,615,695 A | 10/1986 | Cooper |
| 4,617,022 A | 10/1986 | Pigneul et al. |
| 4,619,649 A | 10/1986 | Roberts |
| 4,623,339 A | 11/1986 | Ciraldo et al. |
| 4,630,320 A | 12/1986 | Van Gompel |
| 4,663,220 A | 5/1987 | Wisneski et al. |
| 4,675,918 A | 6/1987 | O'Brien |
| D290,780 S | 7/1987 | Wistrand |
| 4,699,622 A | 10/1987 | Toussant et al. |
| 4,704,116 A | 11/1987 | Enloe |
| 4,726,874 A | 2/1988 | Van Vliet |
| 4,728,326 A | 3/1988 | Gilles |
| 4,743,239 A | 5/1988 | Cole |
| 4,747,846 A | 5/1988 | Boland et al. |
| 4,753,646 A | 6/1988 | Enloe |
| 4,753,650 A | 6/1988 | Williams |
| 4,798,603 A | 1/1989 | Meyer et al. |
| 4,801,485 A | 1/1989 | Sallee et al. |
| 4,808,252 A | 2/1989 | Lash |
| 4,826,499 A | 5/1989 | Ahr |
| 4,850,988 A | 7/1989 | Aledo et al. |
| 4,850,992 A | 7/1989 | Amaral et al. |
| 4,857,067 A | 8/1989 | Wood et al. |
| 4,883,481 A | 11/1989 | Blanchard |
| 4,892,598 A | 1/1990 | Stevens et al. |
| 4,895,569 A | 1/1990 | Wilson et al. |
| 4,904,252 A | 2/1990 | Fitzgerald |
| 4,908,247 A | 3/1990 | Baird et al. |
| 4,909,802 A | 3/1990 | Ahr et al. |
| 4,911,702 A | 3/1990 | O'Leary et al. |
| 4,917,682 A | 4/1990 | Lancaster et al. |
| 4,936,840 A | 6/1990 | Proxmire |
| 4,937,887 A | 7/1990 | Schreiner |
| 4,938,753 A | 7/1990 | Van Gompel et al. |
| 4,944,733 A | 7/1990 | Casale |
| 4,961,736 A | 10/1990 | McCloud |
| 4,964,860 A | 10/1990 | Gipson et al. |
| 4,973,326 A | 11/1990 | Wood et al. |
| 4,988,346 A | 1/1991 | Pfefferkorn |
| 4,998,929 A | 3/1991 | Bjorksund et al. |
| 5,019,072 A | 5/1991 | Polski |
| 5,019,073 A | 5/1991 | Roessler et al. |
| 5,040,244 A | 8/1991 | Tubbs |
| 5,062,839 A | 11/1991 | Anderson |
| 5,066,289 A | 11/1991 | Polski |
| 5,069,678 A | 12/1991 | Yamamoto et al. |
| 5,074,854 A | 12/1991 | Davis |
| 5,087,253 A | 2/1992 | Cooper |
| 5,106,382 A | 4/1992 | Henry |
| 5,106,385 A | 4/1992 | Allen et al. |
| 5,110,403 A | 5/1992 | Ehlert |
| 5,112,326 A | 5/1992 | Quadrini |
| 5,135,522 A | 8/1992 | Fahrenkrug et al. |
| 5,140,757 A | 8/1992 | Terada |
| 5,163,932 A | 11/1992 | Nomura et al. |
| 5,170,505 A | 12/1992 | Rohrer |
| 5,176,668 A | 1/1993 | Bernardin |
| 5,176,670 A * | 1/1993 | Roessler et al. ........ 604/385.21 |
| 5,176,672 A | 1/1993 | Bruemmer et al. |
| 5,185,011 A | 2/1993 | Strasser |
| 5,186,779 A | 2/1993 | Tubbs |
| 5,187,817 A | 2/1993 | Zolner |
| 5,192,606 A | 3/1993 | Proxmire et al. |
| 5,226,992 A | 7/1993 | Morman |
| 5,236,430 A | 8/1993 | Bridges |
| 5,242,436 A | 9/1993 | Weil et al. |
| 5,246,433 A | 9/1993 | Hasse et al. |
| 5,275,590 A | 1/1994 | Huffman et al. |
| 5,300,057 A | 4/1994 | Miller et al. |
| 5,304,162 A | 4/1994 | Kuen |
| 5,312,387 A | 5/1994 | Rossini et al. |
| 5,340,431 A | 8/1994 | Terada |
| 5,358,500 A | 10/1994 | Lavon et al. |
| 5,368,584 A | 11/1994 | Clear et al. |
| 5,368,585 A | 11/1994 | Dokken |
| 5,370,632 A | 12/1994 | Beplate |
| 5,370,634 A | 12/1994 | Ando et al. |
| 5,373,587 A | 12/1994 | Sexton |
| 5,374,262 A | 12/1994 | Keuhn, Jr. et al. |
| 5,383,872 A | 1/1995 | Roessler et al. |
| 5,386,595 A | 2/1995 | Kuen et al. |
| 5,397,639 A | 3/1995 | Tollini |
| 5,399,219 A | 3/1995 | Roessler et al. |
| 5,401,275 A | 3/1995 | Flug et al. |
| 5,409,476 A | 4/1995 | Coates |
| 5,423,789 A | 6/1995 | Kuen |
| 5,445,628 A | 8/1995 | Gipson et al. |
| 5,451,219 A | 9/1995 | Suzuki et al. |
| 5,462,541 A | 10/1995 | Bruemmer et al. |
| 5,489,282 A | 2/1996 | Zehner et al. |
| 5,496,298 A | 3/1996 | Kuepper et al. |
| 5,499,978 A | 3/1996 | Buell et al. |
| 5,500,063 A | 3/1996 | Jessup |
| 5,509,915 A | 4/1996 | Hanson et al. |

| Patent No. | Date | Inventor |
|---|---|---|
| 5,527,302 A | 6/1996 | Endres et al. |
| H1558 H | 7/1996 | Goulait et al. |
| 5,531,731 A | 7/1996 | Brusky |
| 5,531,732 A | 7/1996 | Wood |
| 5,537,722 A | 7/1996 | Niederhofer et al. |
| 5,540,796 A | 7/1996 | Fries |
| 5,545,158 A | 8/1996 | Jessup |
| 5,545,275 A | 8/1996 | Herrin et al. |
| 5,549,592 A | 8/1996 | Fries et al. |
| 5,554,146 A | 9/1996 | Niederhofer et al. |
| 5,562,650 A | 10/1996 | Everett et al. |
| 5,569,232 A | 10/1996 | Roe et al. |
| 5,569,234 A | 10/1996 | Buell et al. |
| 5,571,586 A | 11/1996 | Gobran |
| 5,575,784 A | 11/1996 | Ames-Ooten et al. |
| 5,582,606 A | 12/1996 | Bruemmer et al. |
| 5,591,152 A | 1/1997 | Buell et al. |
| 5,593,401 A | 1/1997 | Sosalla et al. |
| 5,601,546 A | 2/1997 | Tanji et al. |
| 5,605,735 A | 2/1997 | Zehner et al. |
| 5,607,416 A | 3/1997 | Yamamoto et al. |
| 5,611,789 A | 3/1997 | Seth |
| 5,618,366 A | 4/1997 | Suekane |
| 5,624,420 A | 4/1997 | Bridges et al. |
| 5,624,424 A | 4/1997 | Saisaka et al. |
| 5,624,428 A | 4/1997 | Sauer |
| 5,624,429 A | 4/1997 | Long et al. |
| 5,626,574 A | 5/1997 | Sasaki et al. |
| 5,628,738 A | 5/1997 | Suekane |
| 5,629,063 A | 5/1997 | Gobran |
| 5,634,916 A | 6/1997 | Lavon et al. |
| H1674 H | 8/1997 | Ames et al. |
| 5,656,111 A | 8/1997 | Dilnik et al. |
| 5,662,637 A | 9/1997 | Kitaoka et al. |
| 5,662,638 A | 9/1997 | Johnson et al. |
| 5,665,084 A | 9/1997 | Richmond |
| 5,669,897 A | 9/1997 | Lavon et al |
| 5,685,873 A | 11/1997 | Bruemmer |
| 5,685,874 A | 11/1997 | Buell et al. |
| 5,690,626 A | 11/1997 | Suzuki et al. |
| 5,690,627 A | 11/1997 | Clear et al. |
| 5,693,038 A | 12/1997 | Suzuki et al. |
| 5,695,488 A | 12/1997 | Sosalla |
| 5,695,868 A | 12/1997 | McCormack |
| D389,320 S | 1/1998 | Vinnage et al. |
| 5,707,364 A | 1/1998 | Coates |
| 5,711,832 A | 1/1998 | Glaug et al. |
| 5,725,518 A | 3/1998 | Coates |
| 5,759,317 A | 6/1998 | Justmann |
| 5,772,649 A * | 6/1998 | Siudzinski ............... 604/386 |
| 5,772,825 A | 6/1998 | Schmitz |
| 5,788,685 A | 8/1998 | Ronnberg et al. |
| 5,788,797 A | 8/1998 | Herrin et al. |
| 5,795,433 A | 8/1998 | Niedermeyer |
| 5,827,259 A | 10/1998 | Laux et al. |
| 5,827,260 A | 10/1998 | Suzuki et al. |
| 5,830,206 A | 11/1998 | Larsson |
| 5,843,056 A | 12/1998 | Good et al. |
| 5,855,574 A | 1/1999 | Kling et al. |
| 5,876,531 A | 3/1999 | Jacobs et al. |
| 5,897,545 A | 4/1999 | Kline et al. |
| 5,899,896 A | 5/1999 | Suprise et al. |
| 5,904,673 A * | 5/1999 | Roe et al. ............... 604/385.3 |
| 5,904,802 A | 5/1999 | Niedermeyer |
| 5,916,203 A * | 6/1999 | Brandon et al. ............ 604/367 |
| 5,916,207 A | 6/1999 | Toyoda et al. |
| 5,919,334 A | 7/1999 | Niedermeyer |
| 5,938,652 A * | 8/1999 | Sauer ................... 604/385.29 |
| 5,944,707 A | 8/1999 | Ronn |
| 5,961,761 A * | 10/1999 | Heindel et al. ............ 156/163 |
| 5,971,153 A | 10/1999 | Bauer et al. |
| 6,022,430 A * | 2/2000 | Blenke et al. ............. 156/73.1 |
| 6,022,431 A * | 2/2000 | Blenke et al. ............. 156/73.1 |
| 6,022,432 A * | 2/2000 | Elsberg et al. ............. 156/73.1 |
| 6,030,373 A | 2/2000 | VanGompel et al. |
| 6,036,805 A | 3/2000 | McNichols |
| 6,045,543 A | 4/2000 | Pozniak et al. |
| 6,113,717 A | 9/2000 | Vogt et al. |
| 6,149,638 A * | 11/2000 | Vogt et al. ............. 604/385.01 |
| 6,287,287 B1 | 9/2001 | Elsberg |
| 6,322,552 B1 | 11/2001 | Blenke et al. |
| 6,336,922 B1 * | 1/2002 | VanGompel et al. ... 604/385.29 |
| 6,361,527 B1 * | 3/2002 | Van Gompel et al. .. 604/385.25 |

FOREIGN PATENT DOCUMENTS

| | | |
|---|---|---|
| CA | 2187366 A1 | 10/1995 |
| EP | 0 206 208 B1 | 12/1986 |
| EP | 0 217 032 A2 | 4/1987 |
| EP | 0 251 251 A3 | 1/1988 |
| EP | 0 463 276 A1 | 1/1992 |
| EP | 0 532 034 A2 | 3/1993 |
| EP | 0 544 703 B1 | 6/1993 |
| EP | 0 696 911 B1 | 2/1996 |
| EP | 0 753 292 A2 | 1/1997 |
| EP | 0 487 758 B1 | 3/1997 |
| EP | 0 597 331 | 11/1997 |
| EP | 0 809 992 A1 | 12/1997 |
| EP | 0 878 180 A2 | 11/1998 |
| FR | 2566631 | 3/1984 |
| GB | 1 520 740 | 8/1978 |
| GB | 2 244 422 B | 12/1991 |
| GB | 2 267 024 B | 11/1993 |
| GB | 2 288 314 A | 10/1995 |
| GB | 2 288 315 A | 10/1995 |
| GB | 2 288 316 A | 10/1995 |
| GB | 2 291 783 A | 2/1996 |
| GB | 2 294 867 A | 5/1996 |
| GB | 2 297 473 A | 6/1996 |
| GB | 2 308 290 | 6/1999 |
| JP | 6-77718 U | 11/1994 |
| JP | 7-213553 A | 8/1995 |
| JP | 7-227407 A | 8/1995 |
| JP | 7-255773 A | 10/1995 |
| JP | 7-299094 A | 11/1995 |
| JP | 8-229072 A | 9/1996 |
| JP | 9-287 U | 5/1997 |
| JP | 11-47188 A | 2/1999 |
| WO | WO 83/04163 A1 | 12/1983 |
| WO | WO 90/07313 A1 | 7/1990 |
| WO | WO 91/04724 A1 | 4/1991 |
| WO | WO 91/08725 A1 | 6/1991 |
| WO | WO 92/22274 A1 | 12/1992 |
| WO | WO 93/09742 A1 | 5/1993 |
| WO | WO 94/17768 A1 | 8/1994 |
| WO | WO 95/01148 A1 | 1/1995 |
| WO | WO 95/02383 A1 | 1/1995 |
| WO | WO 95/13772 A1 | 5/1995 |
| WO | WO 95/22951 A1 | 8/1995 |
| WO | WO 95/27460 A1 | 10/1995 |
| WO | WO 95/27462 A1 | 10/1995 |
| WO | WO 95/29657 A1 | 11/1995 |
| WO | WO 96/03101 A1 | 2/1996 |
| WO | WO 96/18315 A1 | 6/1996 |
| WO | WO 96/29037 | 9/1996 |
| WO | WO 96/32084 A1 | 10/1996 |
| WO | WO 97/15260 A1 | 5/1997 |
| WO | WO 97/23186 A1 | 7/1997 |
| WO | WO 97/25951 A1 | 7/1997 |
| WO | WO 97/31605 A1 | 9/1997 |
| WO | WO 97/32555 A1 | 9/1997 |
| WO | WO 97/33547 A1 | 9/1997 |
| WO | WO 97/46197 A1 | 12/1997 |

| | | |
|---|---|---|
| WO | WO 97/47265 | 12/1997 |
| WO | WO 97/48357 | 12/1997 |
| WO | WO 98/03140 A1 | 1/1998 |
| WO | WO 98/18421 A1 | 5/1998 |
| WO | WO 98/29251 | 7/1998 |
| WO | WO 98/51252 | 11/1998 |
| WO | WO 98/56328 A1 | 12/1998 |
| WO | WO 99/07319 A1 | 2/1999 |
| WO | WO 99/56688 | 11/1999 |
| WO | WO 99/65438 | 12/1999 |
| WO | WO 99/65442 | 12/1999 |
| WO | WO 00/0037010 | 6/2000 |
| WO | WO 01/43682 A1 | 6/2001 |
| WO | WO 01/43683 A1 | 6/2001 |
| WO | WO 01/70155 A1 | 9/2001 |

OTHER PUBLICATIONS

Derwent World Patent Database abstract of JP 95–044941 B2: Description of ZUIKO KK (Kuik–N), "Simple Solid Diaper For Eliminating Waste of Material by Using Square Shape."

Derwent World Patent Database abstract of JP 9–276334 A: Description of Kao Corp (Kaos), "Disposable Baby Nappy."

Derwent World Patent Database abstract of JP 11–070143 A: Description of TOYO EISAI KK (TOEI–N), "Disposable Diaper For Adults And Children."

Derwent World Patent Database abstract of JP 11–076299 A: Description of UNI–CHARM KK (UNIC–N), "Disposable Diaper."

* cited by examiner

PREFASTENED DISPOSABLE ABSORBENT ARTICLES HAVING A STRETCH PANEL

FIELD OF THE INVENTION

The present invention relates to disposable absorbent articles which are adapted to contain body exudates. More particularly, the present invention relates to prefastened absorbent articles having stretch panels for improved fit and performance.

BACKGROUND OF THE INVENTION

It is desired that absorbent articles such as diapers, training pants or incontinence garments provide a close, comfortable fit about the wearer and contain body exudates. Moreover, it is desirable that such absorbent articles, after being soiled, can be removed from the wearer in a convenient and clean manner without undesirably soiling the caregiver or surrounding area such as the clothes of the wearer. In certain circumstances, it is also desirable that such absorbent articles are capable of being pulled up or down over the hips of the wearer to allow the wearer or caregiver to easily pull the article on and easily remove the article if it has not been soiled. For example, such absorbent articles can assist in the toilet training of children.

Conventional diapers have typically included a front waist portion and a rear waist portion, which are releasably connected about the hips of the wearer during use by conventional fasteners such as adhesive tape fasteners or hook and loop type fasteners. For example, the conventional fasteners have typically included a pair of fasteners, such as adhesive tape tabs, located on the outermost corners of the diaper in the rear waist region of the diaper and a complimentary fastener, such as a taping panel, located on the outer surface of the outer cover of the diaper in the front waist portion of the diaper. In such a configuration, the diaper has been positioned between the legs of the wearer while the wearer is lying down and the adhesive tape tabs have been releasably attached to the taping panel to secure the rear waist portion to the front waist portion of the diaper to secure the diaper about the waist of the wearer. Such conventional diapers are easy to fasten about and remove from the wearer after use without undesirably soiling the caregiver. However, such conventional diapers are not provided in a pant-like, prefastened configuration and, thus, are not configured to be pulled up or down over the hips of the wearer when the fasteners are attached. Conventional diapers have also typically included elasticized waistbands to help reduce the leakage of body exudates. Some conventional diapers have also included elasticized containment or barrier flaps at the leg or waist regions of the diaper to further reduce leaks. Further, the fastening systems of some conventional diapers have also been elasticized.

Several attempts have been made to provide absorbent articles which effectively contain body exudates, are capable of being pulled up or down over the hips of the wearer, and provide ease of cleaning and removal after being soiled. For example, some conventional absorbent articles, such as conventional training pants, have included integral side panels which connect the front waist portion to the rear waist portion of the absorbent article. The side panels have been made stretchable such that the waist opening of the absorbent article can expand to allow the absorbent article to be pulled up or down over the hips of the wearer if desired. Such side panels have also been designed such that they may be torn to remove the training pant from the wearer after it has been soiled.

However, many of such attempts have not been completely satisfactory. For example, absorbent articles such as training pants have not always been able to achieve a close conforming fit to the wearer while still being able to expand enough to be pulled up and down over the hips of the wearer. Often such training pants fit the waist of the wearer loosely which can undesirably result in leaks. As a result, many of such articles have not contained bodily exudates as effectively as conventional diaper-type articles which can be adjusted to achieve a more conforming fit to the wearer. Moreover, the inspection and removal of soiled absorbent articles which have integral side panels, such as conventional training pants, have not always been completely satisfactory. For example, the side panels have been difficult to tear when attempting to remove the article from the waist of the wearer instead of pulling the article down over the hips of the wearer.

Further, diapers having elasticized waistbands or flaps at their waist regions and elasticized fastening systems have not been completely satisfactory. For example, such waistbands have generally been narrow and consequently have not always provided a reliable sealing surface with the wearer's body, resulting in leakage. Moreover, although the elasticized fastening systems used on conventional diapers have improved the fit of the diaper about the wearer, such systems have typically not been tied in or connected to the elasticized waistbands and flaps. Thus, the forces exerted on the fastening system have not been efficiently transferred and distributed laterally across the waist region of the diaper along a wide band. As a result, the fit and containment of conventional absorbent articles have not been completely satisfactory.

Accordingly, despite the attempts to develop improved absorbent articles, there remains a need for absorbent articles which can provide the benefits of both conventional training pants and conventional diapers. That is, there remains a need for absorbent articles which conform to the wearer to effectively contain bodily exudates, which are capable of being pulled up and down over the hips and buttocks of the wearer without opening, which are readily secured about and removed from the wearer in a convenient and clean manner, and which allow easy inspection by the care giver to assist in determining whether the article is soiled. Moreover, there remains a need for improved fit and containment at the waist regions of absorbent articles.

SUMMARY OF THE INVENTION

In response to the difficulties and problems discussed above, new prefastened, refastenable, disposable absorbent articles which have a stretch panel have been invented.

In one aspect, the present invention concerns a prefastened, refastenable, disposable absorbent article which comprises an absorbent chassis which defines a front waist region, a rear waist region, a crotch region which extends between and connects the waist regions, a pair of longitudinally opposed end edges, and a pair of laterally opposed side edges. The absorbent article also includes at least one stretch panel which is located in one of the waist regions and which defines a waist edge, a pair of laterally opposed outboard edges which are located laterally beyond both of the side edges of the absorbent chassis, and an inward edge which is located longitudinally inward from the end edge of the absorbent chassis. The absorbent article further includes a pair of primary fasteners which are located on the laterally opposed outboard edges of the stretch panel and which are releasably prefastened to the opposite waist region of the absorbent chassis to releasably engage the front waist region to the rear waist region to provide the prefastened disposable absorbent article.

In a particular aspect, the prefastened absorbent article may further include at least one secondary fastener tab created by a pair of laterally directed perforations on at least one of two laterally opposed sides of the stretch panel. The prefastened absorbent article may further include a pair of passive side bonds which are located inward of the primary fasteners and which releasably connect an overlapped portion of the waist regions to assist in maintaining the prefastened absorbent article in a prefastened condition.

In another particular aspect, the stretch panel may comprise a center bridge panel, and a pair of laterally opposed side panels which are connected to opposed lateral edges of the bridge panel and which extend laterally beyond the side edges of the absorbent chassis. In a particular embodiment, the bridge panel is elastomeric, and the side panels are non-elastomeric.

In still another aspect, the present invention concerns a package of prefastened disposable absorbent articles comprising a container and a plurality of the prefastened absorbent articles. Each prefastened, refastenable, disposable absorbent article comprises an absorbent chassis which defines a front waist region, a rear waist region, a crotch region which extends between and connects the waist regions, a pair of longitudinally opposed end edges, and a pair of laterally opposed side edges. Each absorbent article also includes at least one stretch panel which is located in one of the waist regions and which defines a waist edge, a pair of laterally opposed outboard edges which are located laterally beyond both of the side edges of the absorbent chassis, and an inward edge which is located longitudinally inward from the end edge of the absorbent chassis. Each absorbent article further includes a pair of primary fasteners which are located on the laterally opposed outboard edges of the stretch panel and which are releasably prefastened to the opposite waist region of the absorbent chassis to releasably engage the front waist region to the rear waist region to provide the prefastened disposable absorbent article.

The present invention advantageously provides prefastened, refastenable, disposable absorbent articles which include a stretch panel. In particular, the present invention provides prefastened disposable absorbent articles which are capable of being reliably pulled up or down over the hips of the wearer to assist in the toilet training of the wearer similar to conventional training pants. Moreover, similar to conventional diapers, the prefastened disposable absorbent articles of the present invention can advantageously be applied to and removed from the wearer similar to conventional diapers after they have been soiled with relative ease and cleanliness. Further, the prefastened disposable absorbent articles of the present invention allow easy inspection by the caregiver to assist in determining whether the article is soiled similar to conventional diapers. Finally, the various aspects of the present invention can advantageously provide an absorbent article having a more contouring fit and improved gasketing about the waist of the wearer, resulting in increased comfort, reduced leakage, and enhanced aesthetics.

BRIEF DESCRIPTION OF THE DRAWINGS

The present invention will be more fully understood and further advantages will become apparent when reference is made to the following detailed description of the invention and the accompanying drawings wherein like numerals represent like elements. The drawings are merely representative and are not intended to limit the scope of the appended claims.

DETAILED DESCRIPTION OF THE INVENTION

The present invention concerns prefastened, refastenable, disposable absorbent articles which are adapted to be worn adjacent to the body of a wearer to absorb and contain various exudates discharged from the body. The prefastened absorbent articles are configured to closely conform to the body of the wearer to effectively contain body exudates while being capable of being pulled up or down over the hips and buttocks of the wearer. The absorbent articles are also refastenable such that they can be secured to and removed directly from the waist of the wearer and easily inspected to determine if they have been soiled during use. As such, the prefastened, refastenable, disposable absorbent articles of the present invention can function in a similar manner to conventional training pants when left in the prefastened configuration or they can be unfastened prior to or during use to function in a refastenable manner similar to conventional diapers. As used herein, the term "disposable" refers to articles which are intended to be discarded after a limited use and which are not intended to be laundered or otherwise restored for reuse.

The prefastened disposable absorbent articles of the present invention will be described in terms of a disposable, prefastened diaper article which is adapted to be worn by infants about the lower torso. In particular, the prefastened disposable absorbent articles will be described in terms of a prefastened, refastenable, disposable diaper having a stretch panel. It is understood that the articles and methods of the present invention are equally adaptable for other types of absorbent articles such as adult incontinent products, training pants, feminine hygiene products, other personal care or health care garments, and the like.

Figure 11:
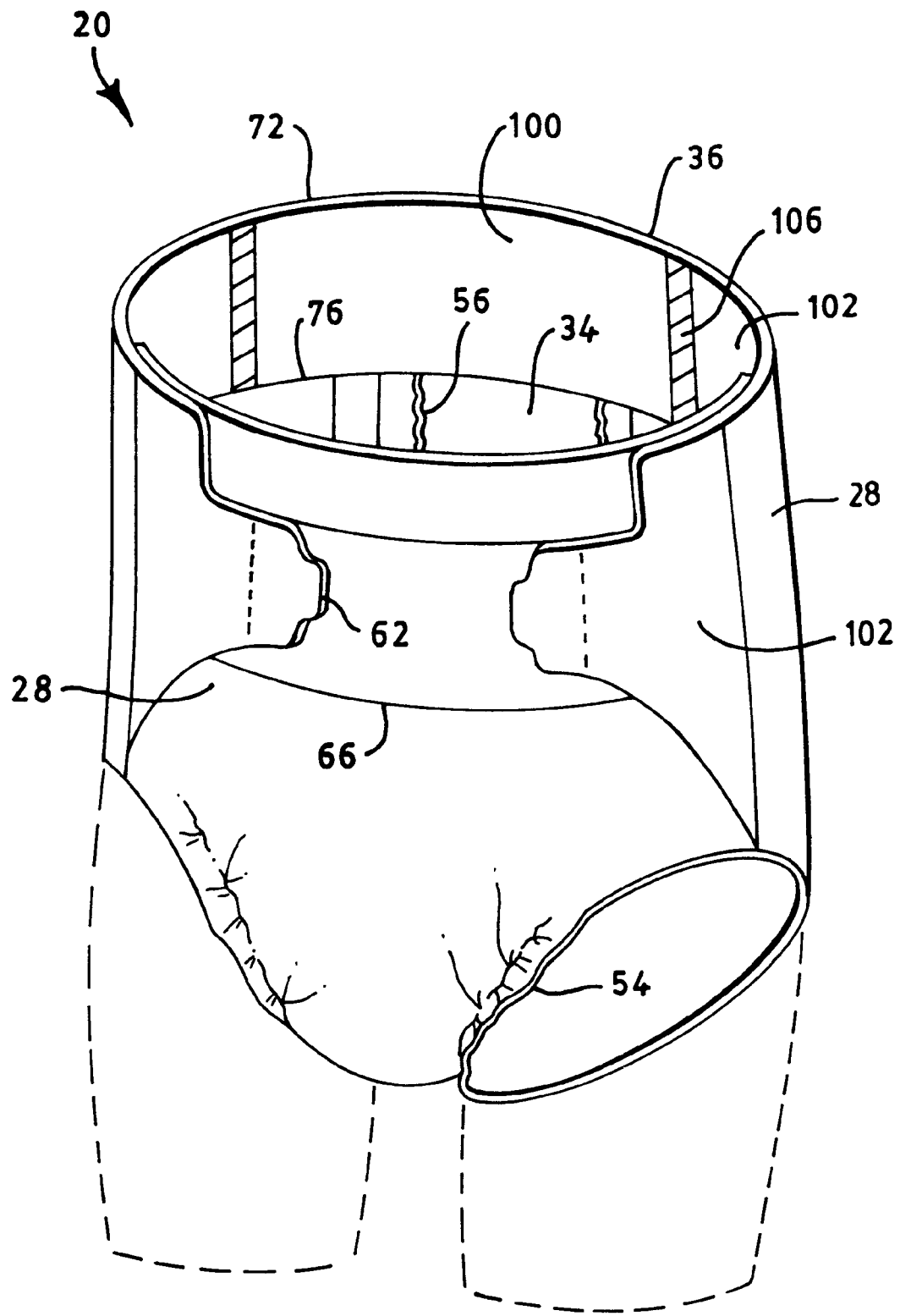
FIG. 11 representatively shows a perspective view of another example of a prefastened disposable absorbent article of the present invention.
Figure 12:
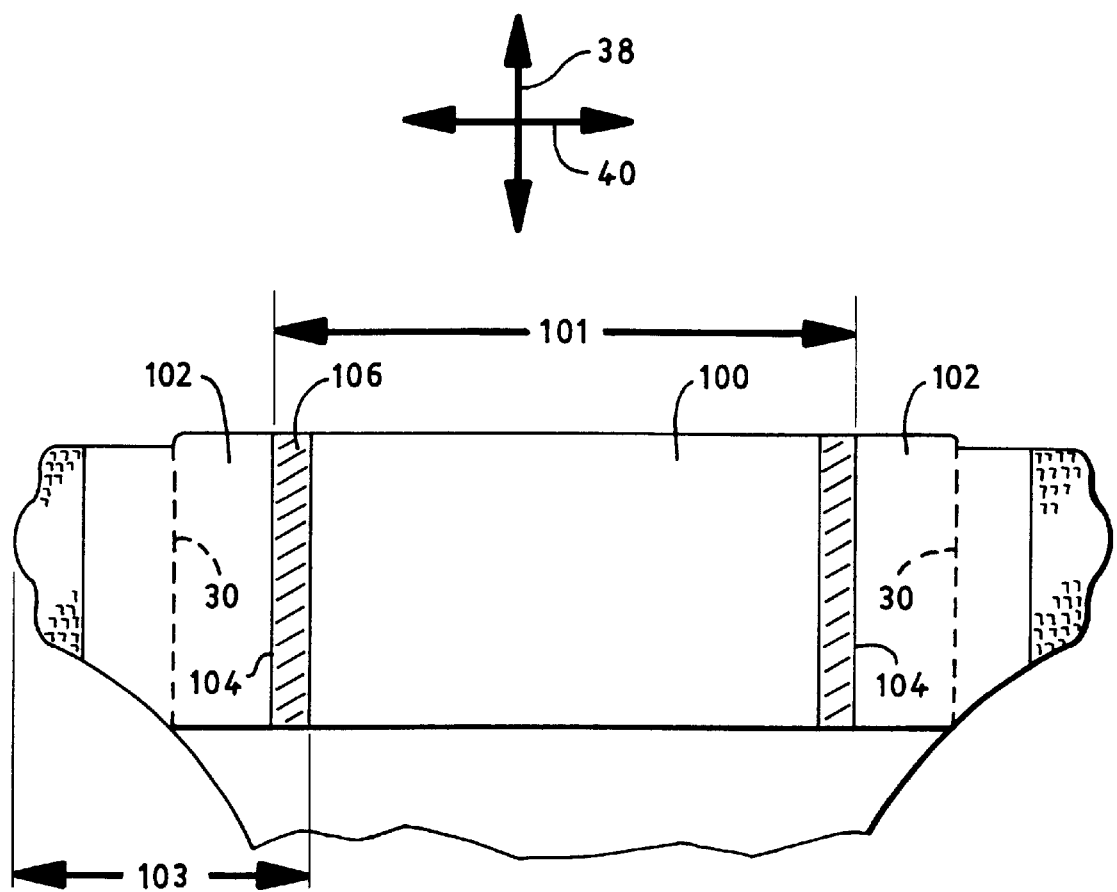
FIG. 12 representatively shows a top plan view of a portion of the prefastened disposable absorbent article of FIG. 11 in an unfastened, stretched, laid-flat condition with the surface of the article which contacts the wearer facing the viewer.
Figure 13:
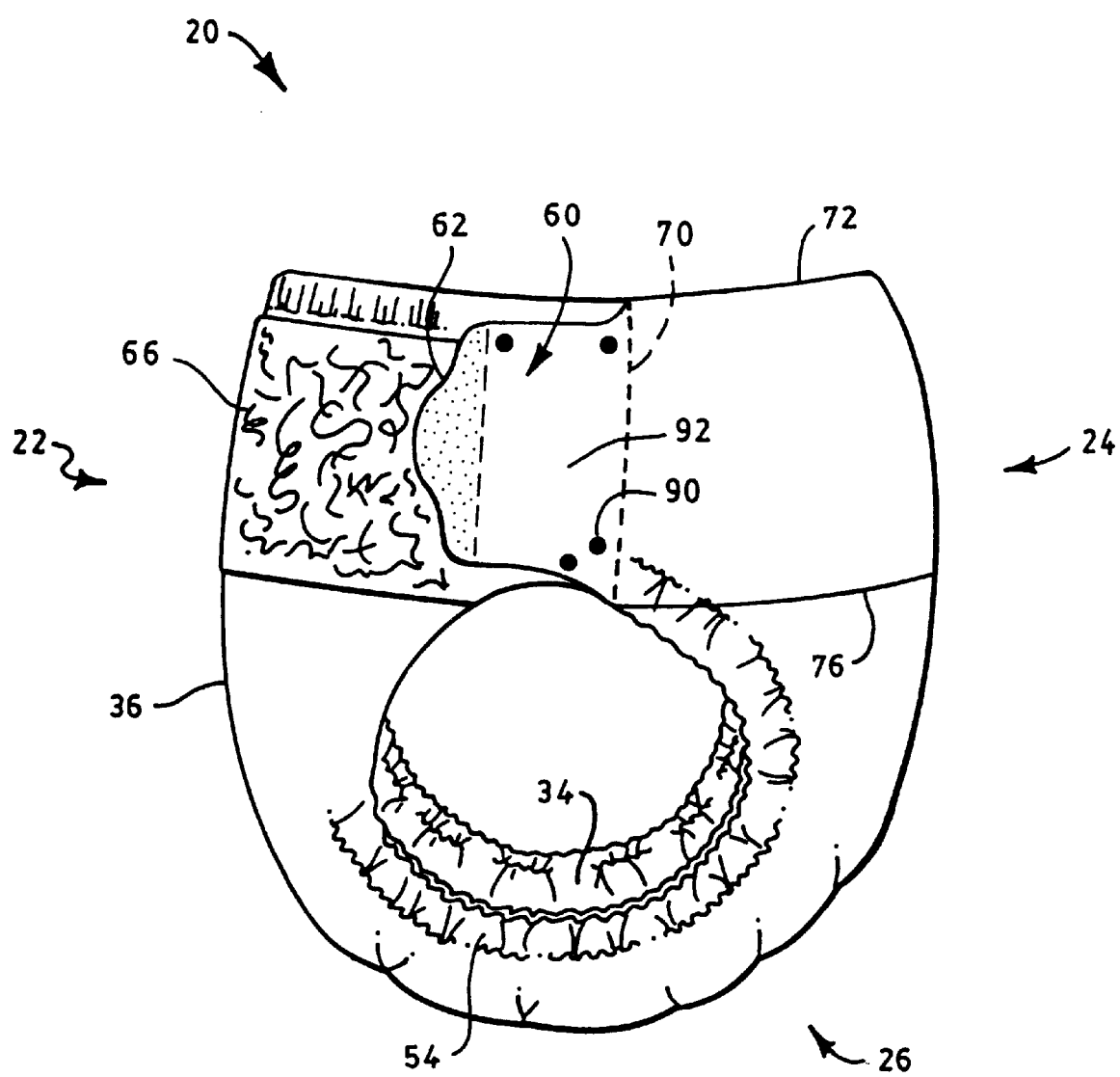
FIG. 13 representatively shows a side view of another example of a prefastened disposable absorbent article of the present invention.
Figure 14:
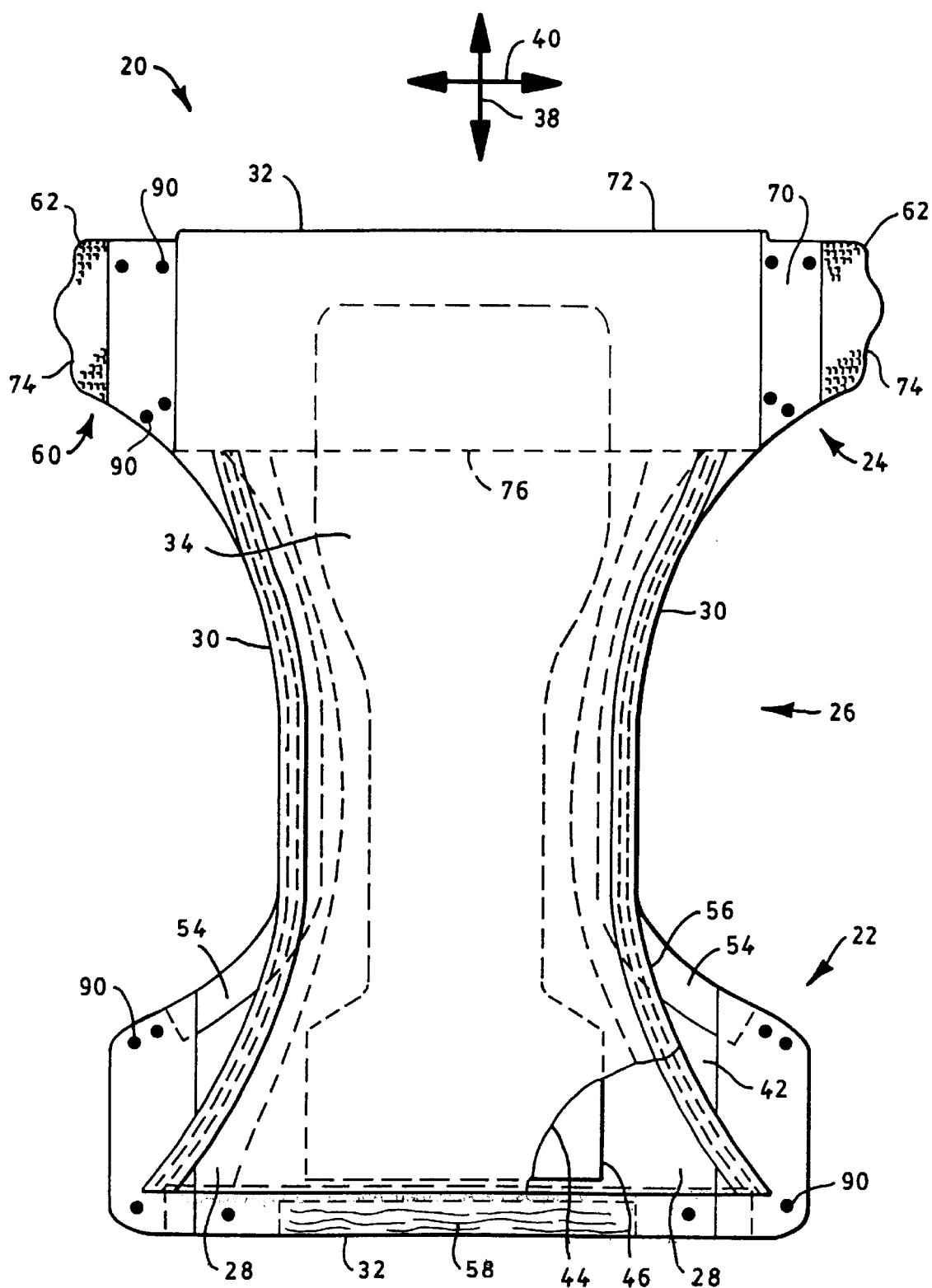
FIG. 14 representatively shows a plan view of the prefastened disposable absorbent article of FIG. 13 in an unfastened, stretched, laid-flat condition with the surface of the article which contacts the wearer facing the viewer and with portions of the absorbent article cut away to show the underlying features.
Figure 15:
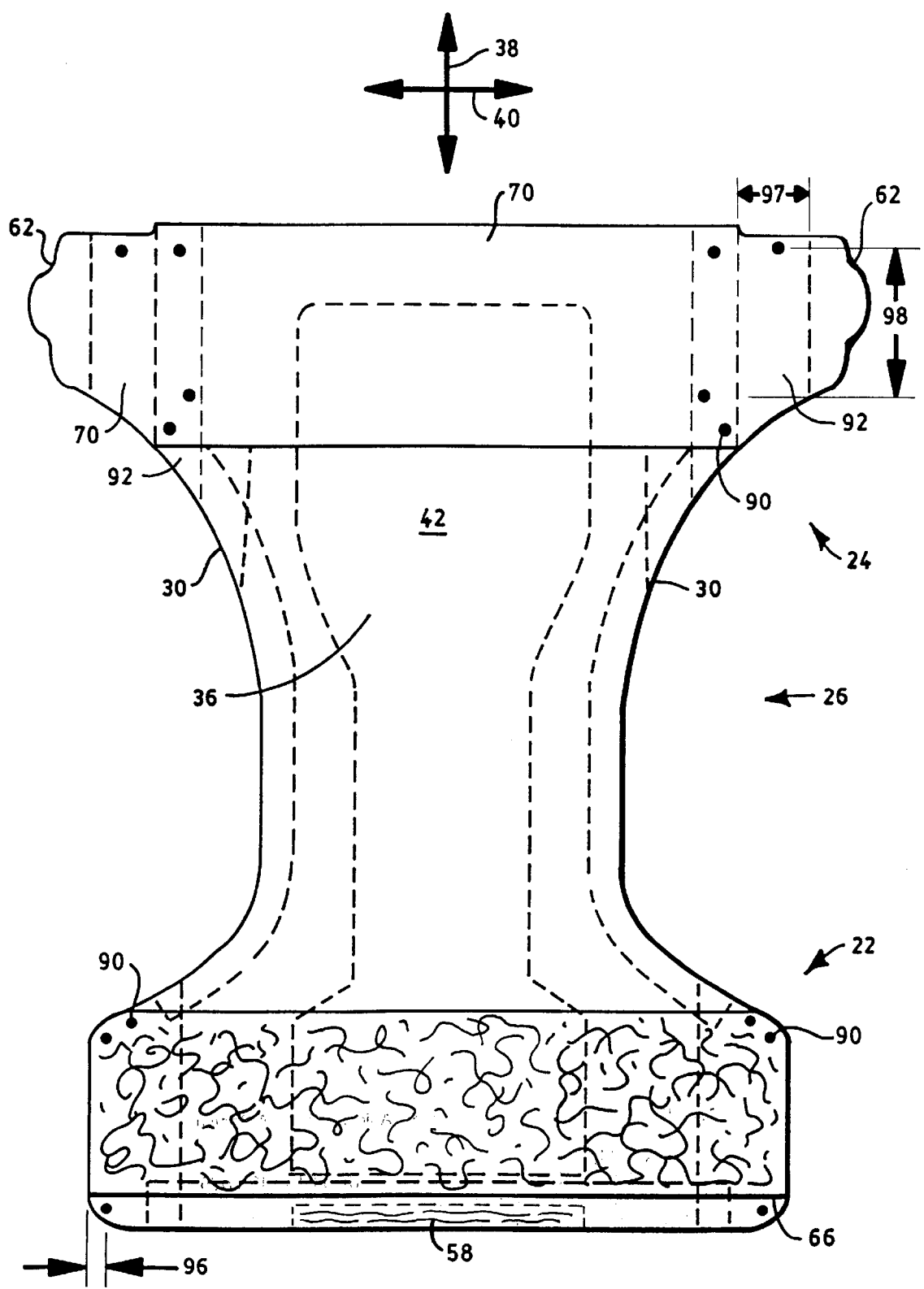
FIG. 15 representatively shows plan view of the prefastened disposable absorbent article of FIG. 13 in an unfastened, stretched, laid-flat condition with the surface of the article which contacts the wearer's clothing facing the viewer.

FIGS. 1–5 representatively show various views of one example of a prefastened, refastenable disposable diaper, as generally indicated at 20, of the present invention. FIGS. 6–10 representatively show various views of another example of a prefastened disposable diaper of the present invention. FIGS. 11–12 representatively show two views of yet another example of a prefastened disposable diaper of the present invention. FIGS. 13–15 representatively show various views of still another example of a prefastened disposable diaper of the present invention.

The illustrated diapers 20 include an absorbent chassis 28 which generally defines a front waist region 22, a rear waist region 24, and a crotch region 26 which extends between and connects the front and rear waist regions 22 and 24. The absorbent chassis 28 further defines a pair of laterally opposed side edges 30, a pair of longitudinally opposed waist edges 32, an interior bodyfacing surface 34 which is configured to contact the wearer, an outer garment facing surface 36 (FIG. 5) opposite the interior surface 34 which is configured to contact the wearer's clothing in use, a longitudinal direction 38, and a lateral direction 40. As representatively illustrated in FIG. 4, the absorbent chassis 28 may include an outer cover 42, a bodyside liner 44 which is connected to the outer cover 42 in a superposed relation, and an absorbent core 46 which is located between the outer cover 42 and the bodyside liner 44.

The front waist region 22 comprises the portion of the diaper 20 which, when worn, is positioned on the front of the wearer while the rear waist region 24 comprises the portion of the diaper 20 which, when worn, is positioned on the back of the wearer. The crotch region 26 comprises the portion of the diaper 20 which, when worn, is positioned between the legs of the wearer and covers the lower torso of the wearer. The laterally opposed side edges 30 of the absorbent chassis 28 of the diaper 20 generally define leg openings which may be curvilinear. The waist edges 32 of the absorbent chassis 28 of the diaper 20 are configured to encircle the waist of the wearer when worn and provide a waist opening when fastened that defines a waist perimeter dimension.

Figure 4:
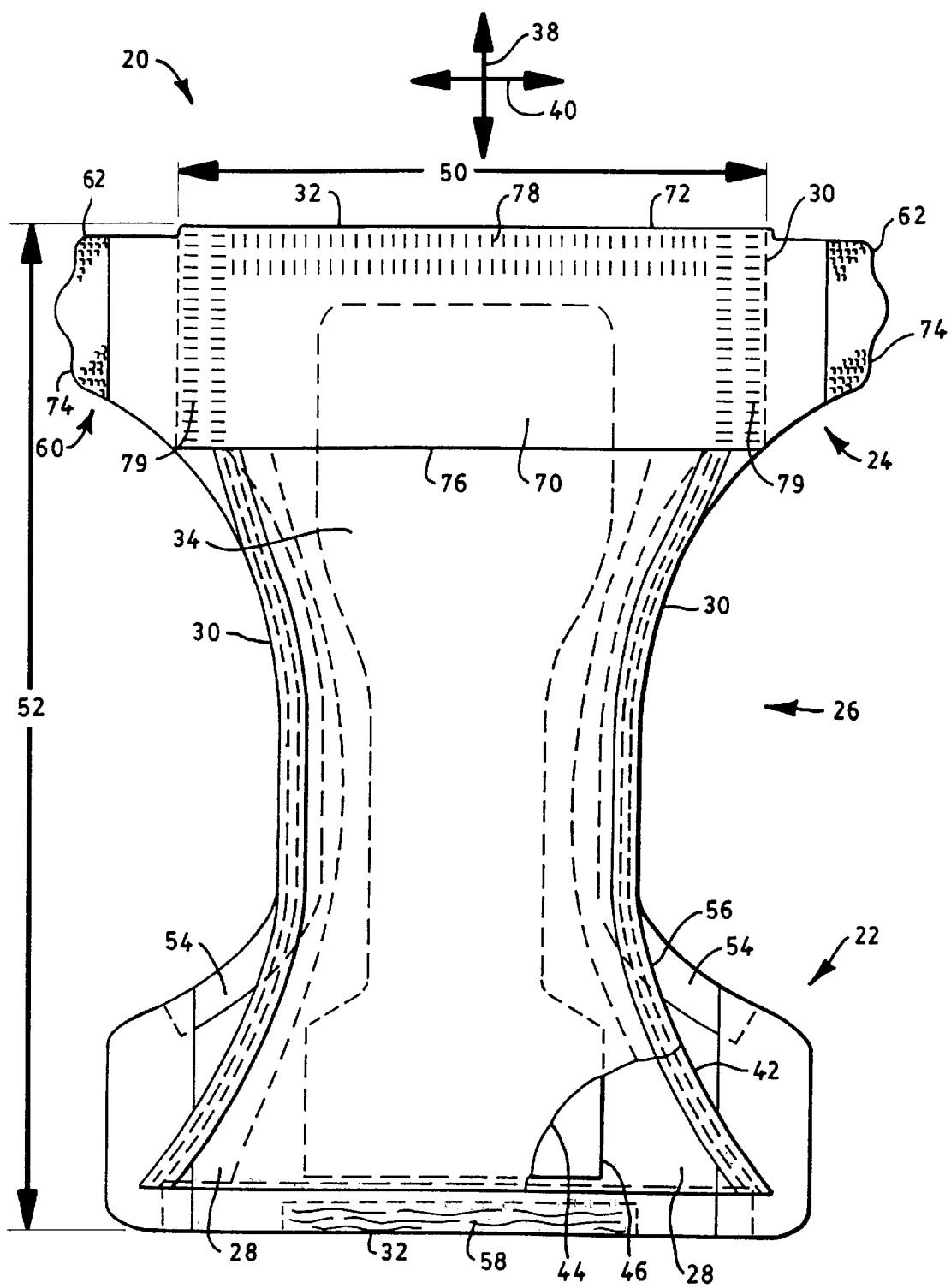
FIG. 4 representatively shows a plan view of the prefastened disposable absorbent article of FIG. 1 in an unfastened, stretched, laid-flat condition with the surface of the article which contacts the wearer facing the viewer and with portions of the article cut away to show the underlying features.

The diaper 20 of the different aspects of the present invention also includes at least one stretch panel 70. For example, as representatively illustrated in FIGS. 1–5, the diaper 20 may include a stretch panel located on the body-facing surface 34 of the absorbent chassis 28 in the rear waist region 24 of the diaper 20. As illustrated in FIG. 4, the stretch panel 70 25 may generally define a waist edge 72, a pair of laterally opposed outboard edges 74 which are located laterally beyond the side edges 30 of the absorbent chassis 28, and an inward edge 76 which is located longitudinally inward from the waist edge 72.

The diaper 20 of the present invention further includes a prefastened, refastenable fastening system 60. The fastening system 60 includes a pair of primary fasteners 62, attached to the laterally opposed outboard edges 74 of the stretch panel 70. As representatively illustrated in FIGS. 1–3, the primary fasteners 62 are releasably engaged with the garment facing surface 36 of the absorbent chassis 28 to provide the prefastened diaper 20. The fastening system 60 may further include an attachment panel 66 located on the outer surface of the absorbent chassis 28 to which the primary fasteners 62 are releasably engaged.

The absorbent chassis 28 is configured to contain and/or absorb any body exudates discharged from the wearer. Whereas, the stretch panel 70 and the prefastened, refastenable fastening system 60 are configured to maintain the diaper 20 about the waist of the wearer and provide a garment-like appearance. The diaper 20 may further include leg elastics 54, containment flaps 56, and waist elastics 58 as are known to those skilled in the art. It should be recognized that individual components of the diaper 20 may be optional depending upon the intended use of the diaper 20.

The diaper 20 may be of various suitable shapes. For example, in the unfastened configuration, the diaper may have an overall rectangular shape, T-shape or an approximately hourglass shape. In the illustrated embodiments, the diaper 20 has a generally hourglass shape in an unfastened configuration. Examples of diaper configurations suitable for use in connection with the instant application and other diaper components suitable for use on diapers are described in U.S. Pat. No. 4,798,603 issued Jan. 17, 1989, to Meyer et al.; U.S. Pat. No. 5,176,668 issued Jan. 5, 1993, to Bernardin; U.S. Pat. No. 5,176,672 issued Jan. 5,1993, to Bruemmer et al.; U.S. Pat. No. 5,192,606 issued Mar. 9, 1993, to Proxmire et al., and U.S. Pat. No. 5,509,915 issued Apr. 23, 1996, to Hanson et al., the disclosures of which are herein incorporated by reference. The various aspects and configurations of the invention can provide distinctive combinations of softness, body conformity, reduced red-marking of the wearer's skin, reduced skin hydration, improved containment of body exudates and improved aesthetics.

The various components of the diaper 20 are integrally assembled together employing various types of suitable attachment means, such as adhesive, sonic and thermal bonds or combinations thereof. In the shown embodiments, for example, the outer cover 42 and bodyside liner 44 are assembled to each other and to the absorbent core 46 with adhesive, such as a hot melt, pressure-sensitive adhesive. The adhesive may be applied as a uniform continuous layer of adhesive, a patterned layer of adhesive, a sprayed pattern of adhesive, or an array of separate lines, swirls or dots of adhesive. Similarly, other diaper components, such as the leg elastic 54 and the primary fasteners 62, may be assembled into the diaper 20 article by employing the above-identified attachment mechanisms. Desirably, the majority of the diaper components are assembled together using ultrasonic bonding techniques for reduced manufacturing cost and improved performance.

Figure 5:
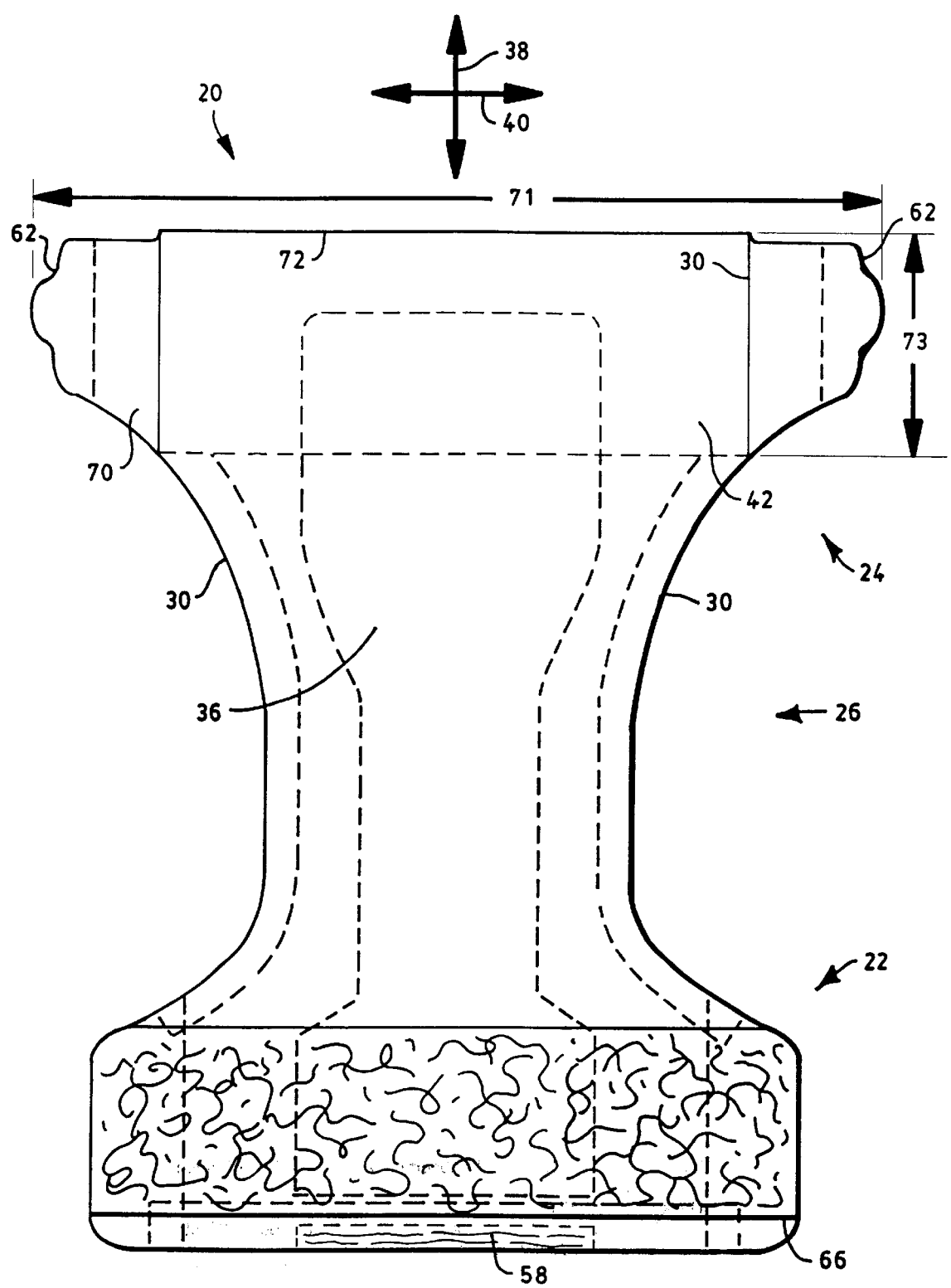
FIG. 5 representatively shows a plan view of the prefastened disposable absorbent article of FIG. 1 in an unfastened, stretched, laid-flat condition with the surface of the article which contacts the wearer's clothing facing the viewer.
Figure 6:
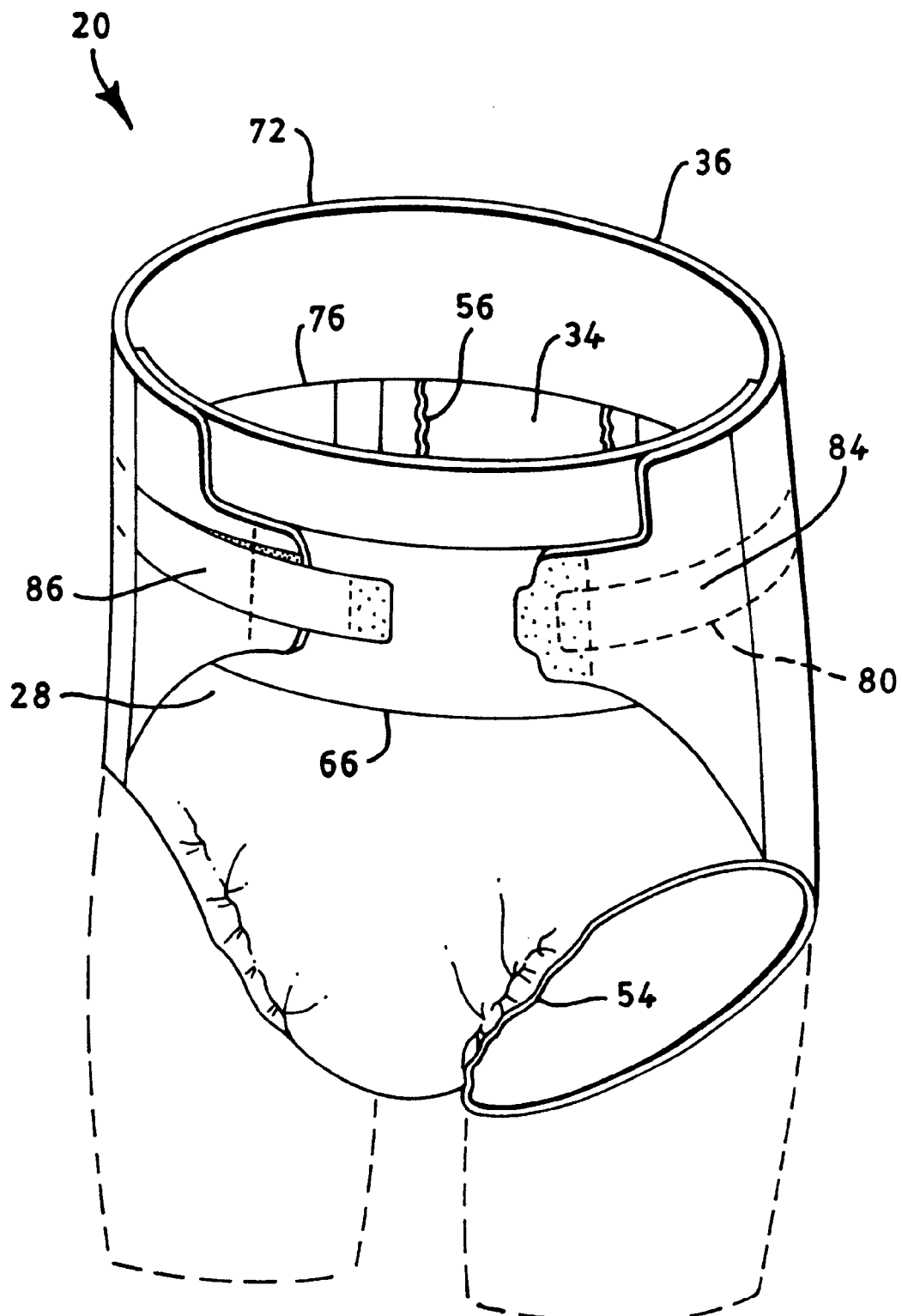
FIG. 6 representatively shows a perspective view of another example of a prefastened disposable absorbent article of the present invention.
Figure 7:
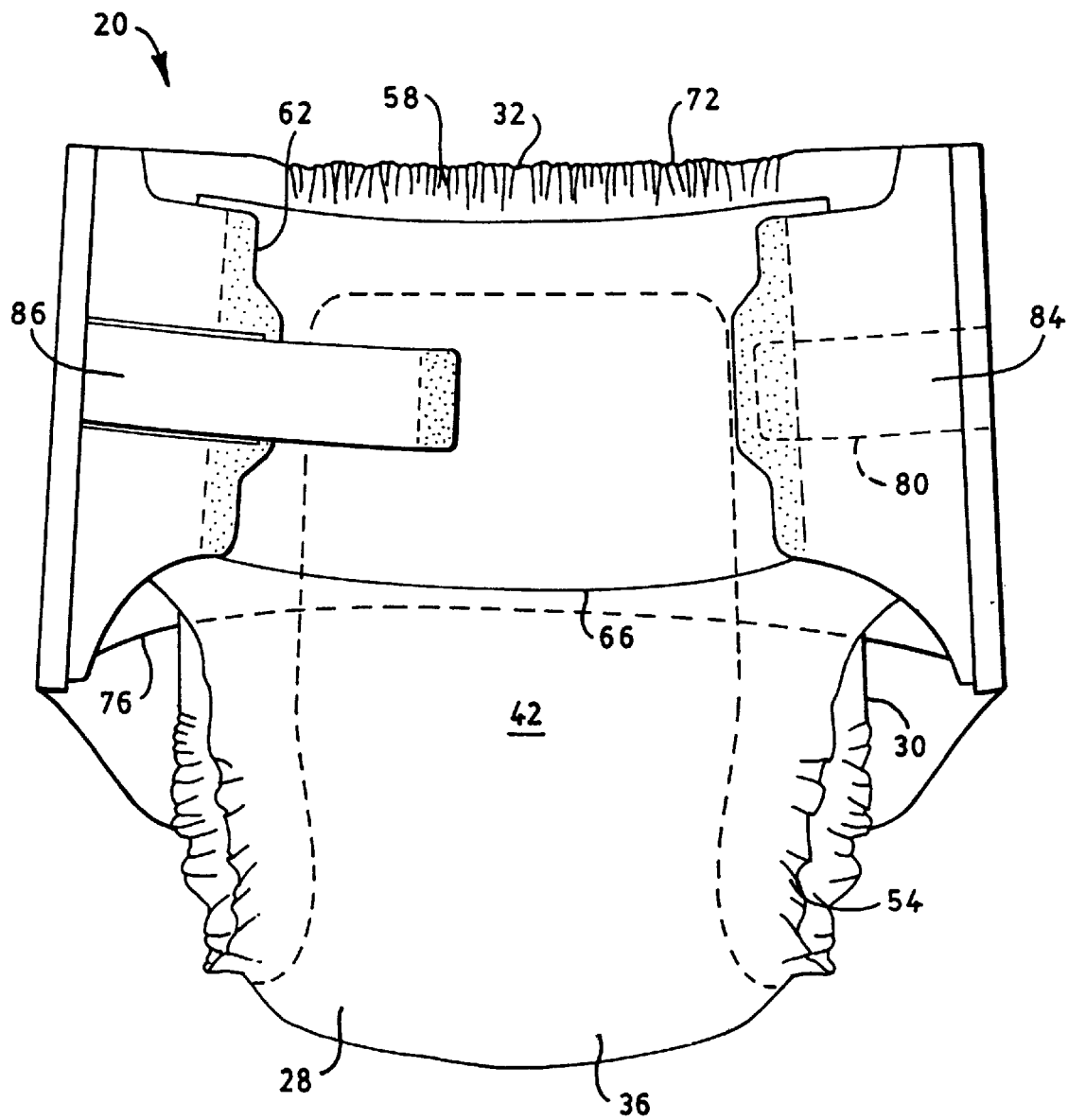
FIG. 7 representatively shows a front plan view of the prefastened disposable absorbent article of FIG. 6.
Figure 8:
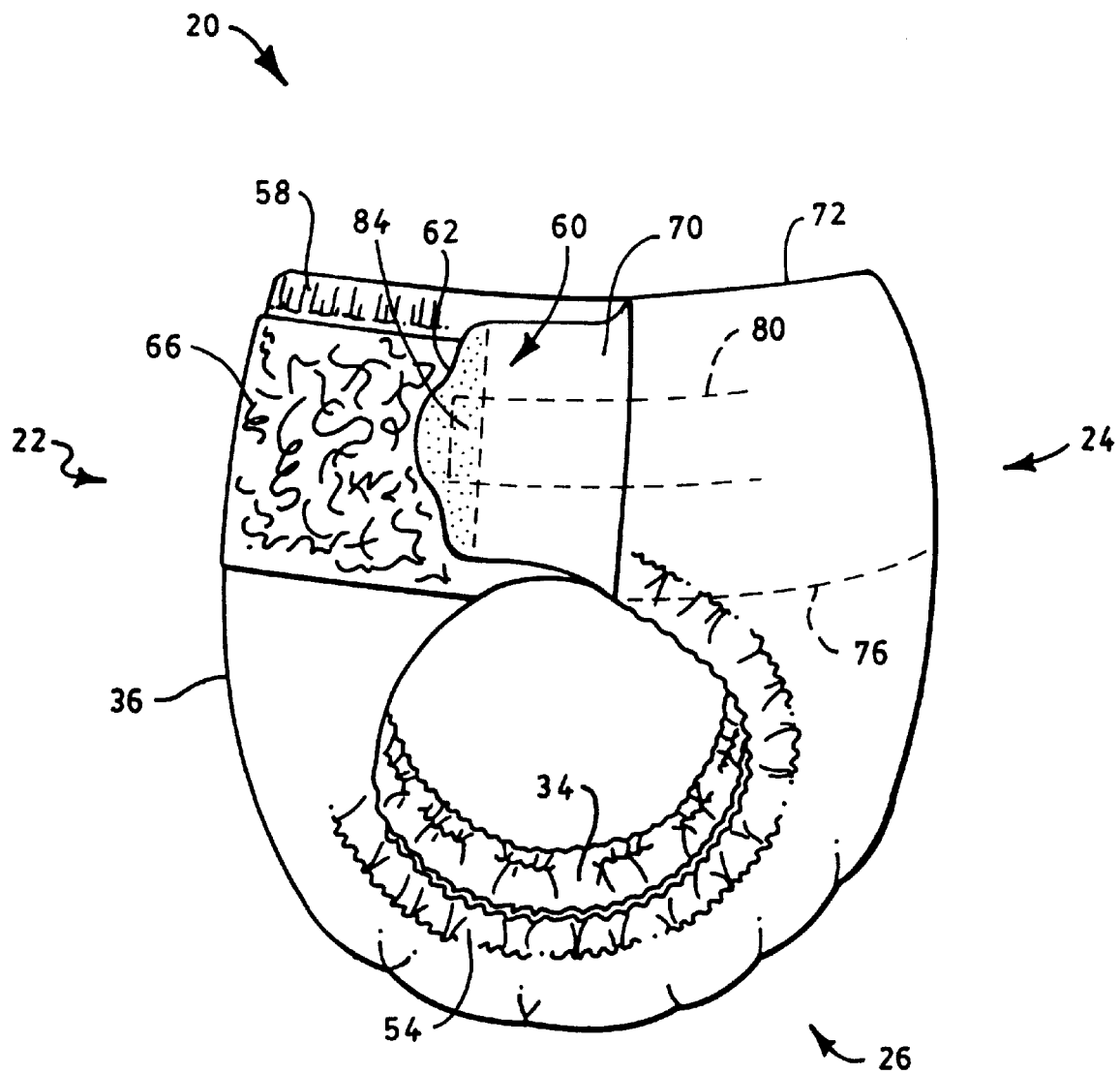
FIG. 8 representatively shows a side view of the prefastened disposable absorbent article of FIG. 6.

The outer cover 42 of the absorbent chassis 28 of the diaper 20, as representatively illustrated in FIGS. 4 and 5, may suitably be composed of a material which is either liquid permeable or liquid impermeable. It is generally preferred that the outer cover 42 be formed from a material that is substantially impermeable to liquids. A typical outer cover can be manufactured from a thin plastic film or other flexible liquid-impermeable material. For example, the outer cover 42 may be formed from a polyethylene film having a thickness of from about 0.013 millimeter (0.5 mil) to about 0.051 millimeter (2.0 mils). If it is desired to present the outer cover 42 with a more clothlike feeling, the outer cover 42 may comprise a polyolefin film having a nonwoven web laminated to the outer surface thereof, such as a spunbond web of polyolefin fibers. For example, a stretch-thinned polypropylene film having a thickness of about 0.015 millimeter (0.6 mil) may have thermally laminated thereto a spunbond web of polypropylene fibers, which fibers have a thickness of about 1.5 to 2.5 denier per filament, which nonwoven web has a basis weight of about 17 grams per square meter (0.5 ounce per square yard). Methods of forming such clothlike outer covers are known to those skilled in the art.

Further, the outer cover 42 may be formed of a woven or nonwoven fibrous web layer which has been totally or partially constructed or treated to impart a desired level of liquid impermeability to selected regions that are adjacent or proximate the absorbent core 46. Still further, the outer cover 42 may optionally be composed of a micro-porous "breathable" material which permits vapors to escape from the absorbent core 46 while still preventing liquid exudates from passing through the outer cover 42. For example, the outer cover 42 may comprise a stretched microporous polyolefin film having a nonwoven web laminated to the outer surface thereof, such as a spunbond web of polyolefin fibers.

The outer cover 42 can also be embossed or otherwise provided with a matte finish to provide a more aesthetically pleasing appearance. Additionally, the outer cover 42 may be comprised of a necked materials such as a necked spunbond web of polyolefin fibers or elasticized nonwoven materials to allow the outer cover 42 to stretch more freely in conjunction with the stretch panel 70. Examples of suitable elasticized materials are stretch-thermal laminate (STL), neck-bonded laminate (NBL), and stretch-bonded laminate (SBL). Methods of making such materials are well known to those skilled in the art and described in U.S. Pat. No. 4,663,220 issued May 5, 1987 to Wisneski et al., U.S. Pat. No. 5,226,992 issued Jul. 13, 1993 to Mormon, and European Patent Application No. EP 0 217 032 published on Apr. 8, 1987 in the names of Taylor et al., the disclosures of which are hereby incorporated as references.

The bodyside liner 44, as representatively illustrated in FIG. 4, suitably presents a bodyfacing surface which is compliant, soft feeling, and nonirritating to the wearer's skin. Further, the bodyside liner 44 may be less hydrophilic than the absorbent core 46, to present a relatively dry surface to the wearer, and may be sufficiently porous to be liquid permeable, permitting liquid to readily penetrate through its thickness. A suitable bodyside liner 44 may be manufactured from a wide selection of web materials, such as porous foams, reticulated foams, apertured plastic films, natural fibers (for example, wood or cotton fibers), synthetic fibers (for example, polyester or polypropylene fibers), or a combination of natural and synthetic fibers. The bodyside liner 44 is suitably employed to help isolate the wearer's skin from liquids held in the absorbent core 46.

Various woven and nonwoven fabrics can be used for the bodyside liner 44. For example, the bodyside liner may be composed of a meltblown or spunbonded web of polyolefin fibers. The bodyside liner may also be a bonded-carded web composed of natural and/or synthetic fibers. The bodyside liner may be composed of a substantially hydrophobic material, and the hydrophobic material may, optionally, be treated with a surfactant or otherwise processed to impart a desired level of wettability and hydrophilicity. In a particular embodiment of the present invention, the bodyside liner 44 comprises a nonwoven, spunbond, polypropylene fabric composed of about 2.8-3.2 denier fibers formed into a web having a basis weight of about 20 grams per square meter and a density of about 0.13 gram per cubic centimeter. The fabric may be surface treated with about 0.3 weight percent of a surfactant commercially available from Hodgson Textile Chemicals, Inc. under the trade designation AHCOVEL Base N-62. The surfactant may be applied by any conventional means, such as spraying, printing, brush coating or the like. The surfactant may be applied to the entire bodyside liner 44 or may be selectively applied to particular sections of the bodyside liner 44, such as the medial section along the longitudinal centerline of the diaper, to provide greater wettability of such sections. The bodyside liner 44 may further include a lotion or treatment applied thereto to which is configured to treat or be transferred to the wearer's skin.

The absorbent core 46 of the diaper 20, as representatively illustrated in FIG. 4, may suitably comprise a matrix of hydrophilic fibers, such as a web of cellulosic fluff, mixed with particles of a high-absorbency material commonly known as superabsorbent material. In a particular embodiment, the absorbent core 46 comprises a matrix of cellulosic fluff, such as wood pulp fluff, and superabsorbent hydrogel-forming particles. The wood pulp fluff may be exchanged with synthetic, polymeric, meltblown fibers or with a combination of meltblown fibers and natural fibers. The superabsorbent particles may be substantially homogeneously mixed with the hydrophilic fibers or may be non-uniformly mixed. The fluff and superabsorbent particles may also be selectively placed into desired zones of the absorbent core 46 to better contain and absorb body exudates. The concentration of the superabsorbent particles may also vary through the thickness of the absorbent core 46. Alternatively, the absorbent core 46 may comprise a laminate of fibrous webs and superabsorbent material or other suitable means of maintaining a superabsorbent material in a localized area.

The absorbent core 46 may have any of a number of shapes. For example, the absorbent core may be rectangular, I-shaped, or T-shaped. It is generally preferred that the absorbent core 46 be narrow in the crotch area of the diaper 20. It has been found that the absorbent chassis 28 of the present invention is particularly useful when the width dimension in the crotch region 26 is from about 2.5 to about 12.7 centimeters (1.0 to about 5.0 inches) and desirably no more than about 7.6 centimeters (3.0 inches). The narrow crotch width dimension of the absorbent chassis 28 allows the absorbent chassis 28 to better fit between the legs of the wearer. The size and the absorbent capacity of the absorbent core 46 should be compatible with the size of the intended wearer and the liquid loading imparted by the intended use of the absorbent article.

The high-absorbency material can be selected from natural, synthetic, and modified natural polymers and materials. The high-absorbency materials can be inorganic materials, such as silica gels, or organic compounds, such as crosslinked polymers. The term "crosslinked" refers to any means for effectively rendering normally water-soluble materials substantially water insoluble but swellable. Such means can include, for example, physical entanglement, crystalline domains, covalent bonds, ionic complexes and associations, hydrophilic associations such as hydrogen bonding, and hydrophobic associations or Van der Waals forces.

Examples of synthetic, polymeric, high-absorbency materials include the alkali metal and ammonium salts of poly (acrylic acid) and poly(methacrylic acid), poly (acrylamides), poly(vinyl ethers), maleic anhydride copolymers with vinyl ethers and alpha-olefins, poly(vinyl pyrolidone), poly(vinyl morpholinone), poly(vinyl alcohol), and mixtures and copolymers thereof. Further polymers suitable for use in the absorbent core include natural and modified natural polymers, such as hydrolyzed acrylonitrile-grafted starch, acrylic acid grafted starch, methyl cellulose, carboxymethyl cellulose, hydroxypropyl cellulose, and the natural gums, such as alginates, xanthum gum, locust bean gum, and the like. Mixtures of natural and wholly or partially synthetic absorbent polymers can also be useful in the present invention. Such high-absorbency materials are well known to those skilled in the art and are widely commercially available. Examples of superabsorbent polymers suitable for use in the present invention are SANWET IM 3900 polymer available from Hoechst Celanese located in Portsmouth, Va. and DOW DRYTECH 2035LD polymer available from Dow Chemical Co. located in Midland, Mich.

The high absorbency material may be in any of a wide variety of geometric forms. As a general rule, it is preferred that the high absorbency material be in the form of discrete particles. However, the high absorbency material may also be in the form of fibers, flakes, rods, spheres, needles, or the like. As a general rule, the high absorbency material is present in the absorbent body in an amount of from about 5 to about 90 weight percent based on total weight of the absorbent core 46.

Optionally, a substantially hydrophilic tissue wrapsheet (not illustrated) may be employed to help maintain the integrity of the airlaid fibrous structure of the absorbent core 46. The tissue wrapsheet is typically placed about the absorbent body over at least the two major facing surfaces thereof and composed of an absorbent cellulosic material, such as creped wadding or a high wet-strength tissue. In one aspect of the invention, the tissue wrapsheet can be configured to provide a wicking layer which helps to rapidly distribute liquid over the mass of absorbent fibers comprising the absorbent body. The wrapsheet material on one side of the absorbent fibrous mass may be bonded to the wrapsheet located on the opposite side of the fibrous mass to effectively entrap the absorbent core 46.

Figure 1:
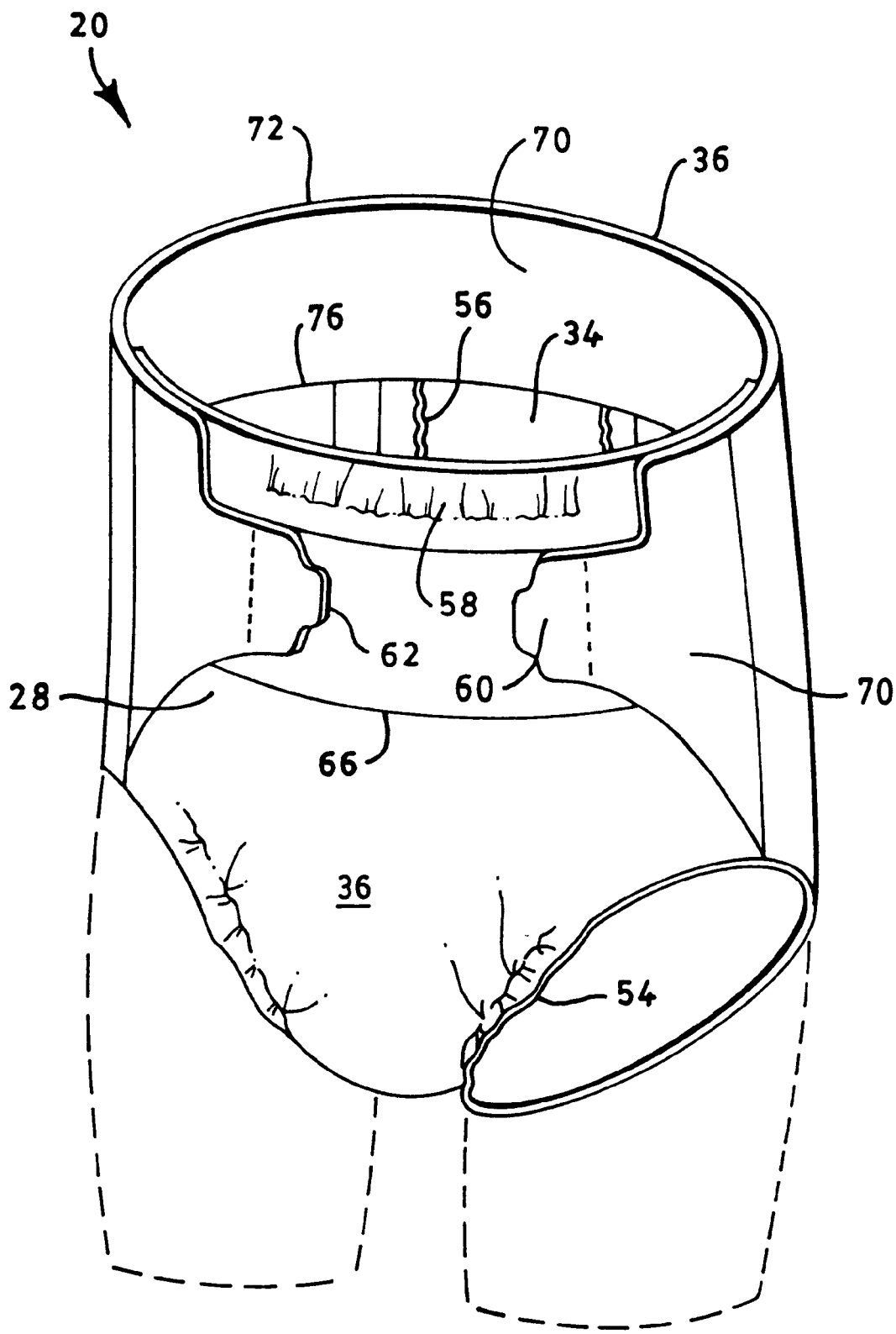
FIG. 1 representatively shows a perspective view of an example of a prefastened disposable absorbent article of the present invention.
Figure 2:
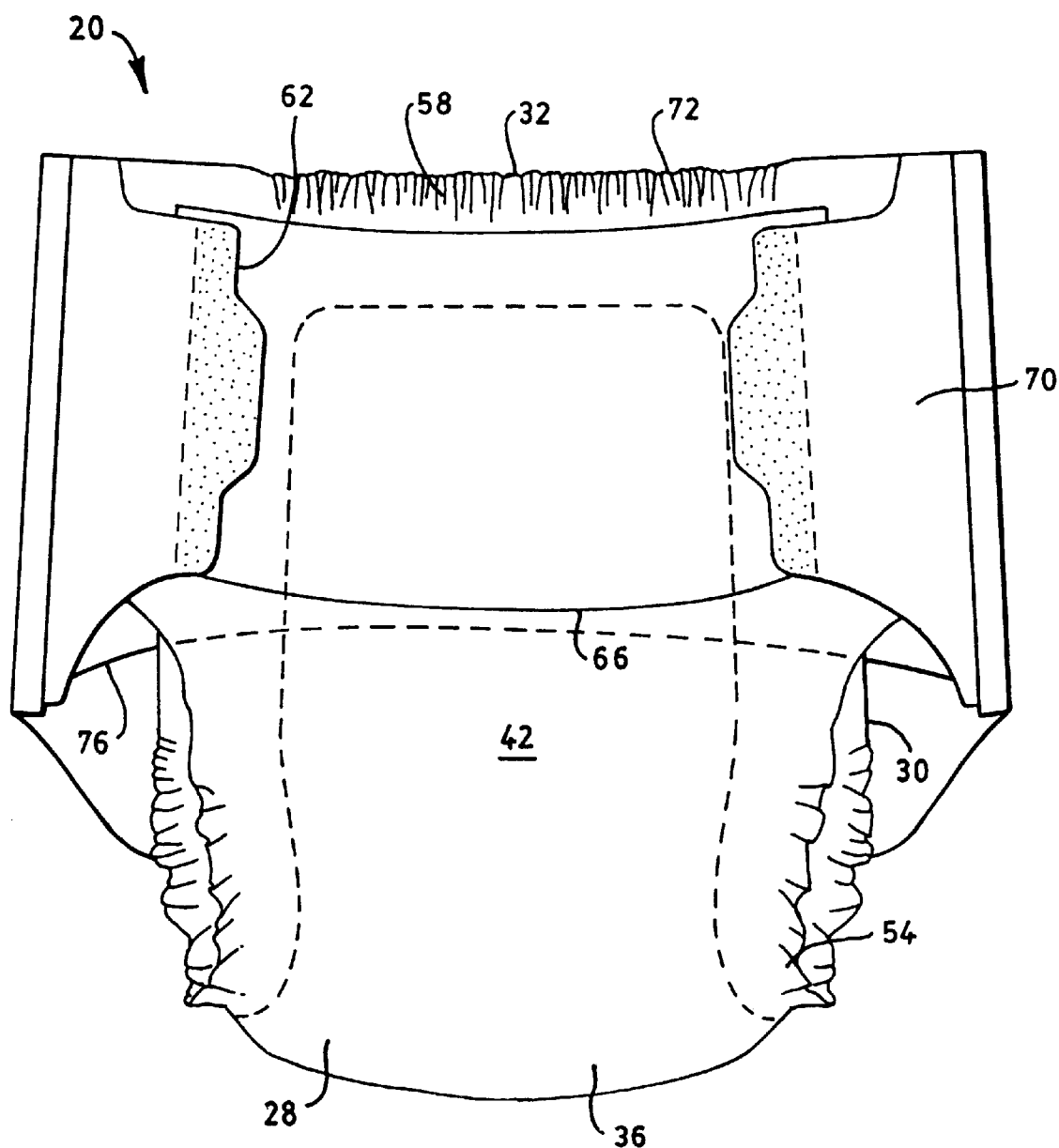
FIG. 2 representatively shows a front plan view of the prefastened disposable absorbent article of FIG. 1.
Figure 3:
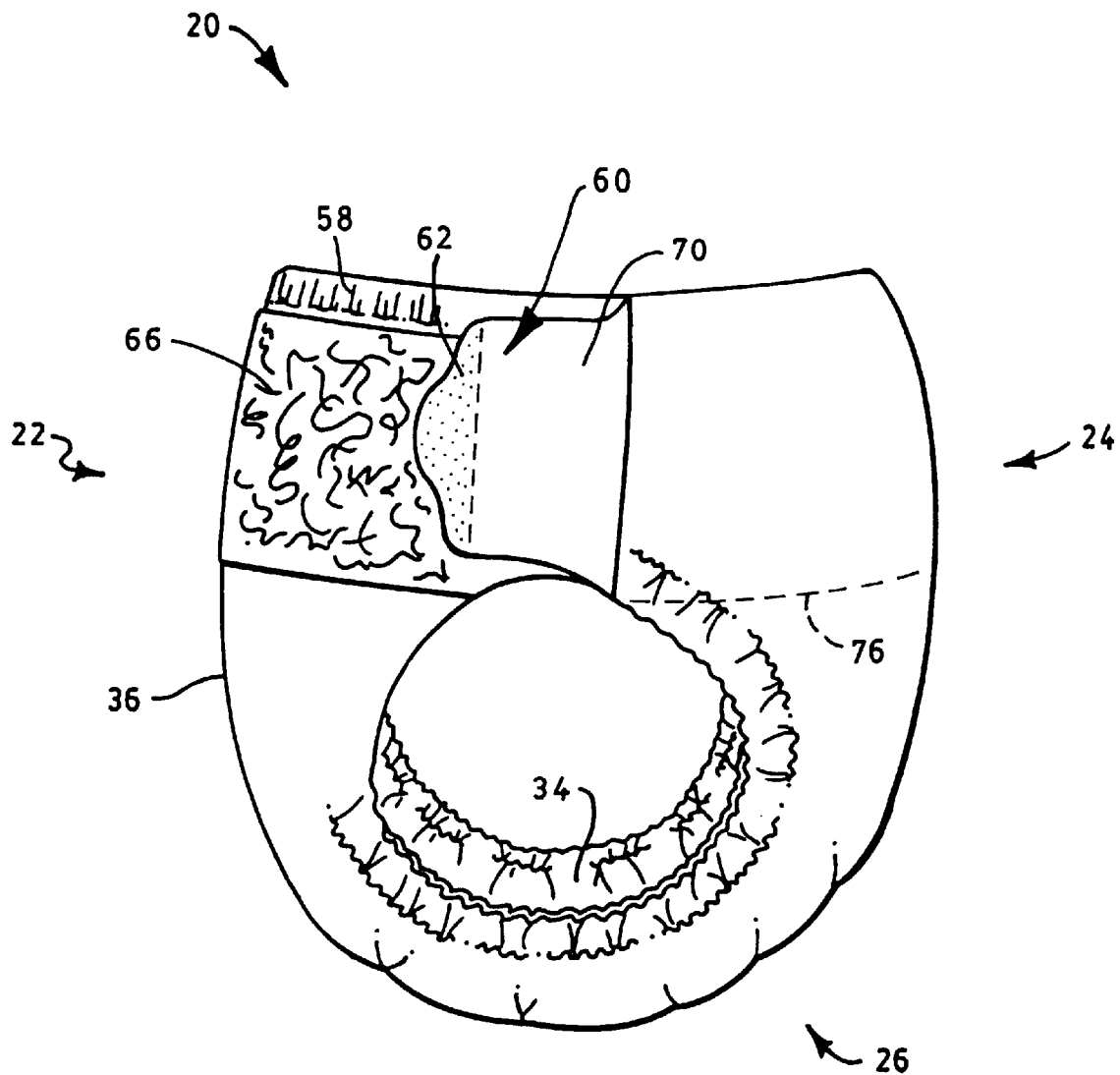
FIG. 3 representatively shows a side view of the prefastened disposable absorbent article of FIG. 1.

As representatively illustrated in FIGS. 1 and 4, the absorbent chassis 28 of the disposable diaper 20 may include a pair of containment flaps 56 which are configured to provide a barrier to the lateral flow of body exudates. The containment flaps 56 may be located along the laterally opposed side edges 30 of the absorbent chassis 28. Each containment flap 56 typically defines an unattached edge which is configured to maintain an upright, perpendicular configuration in at least the crotch region 26 of the diaper 20 to form a seal against the wearer's body. The containment flaps 56 may extend longitudinally along the entire length of the absorbent chassis 28 or may only extend partially along the length of the absorbent chassis 28. When the containment flaps 56 are shorter in length than the absorbent chassis 28, the containment flaps 56 can be selectively positioned anywhere along the side edges 30 of the absorbent chassis 28. In a particular aspect of the invention, the containment flaps 56 extend along the entire length of the absorbent chassis 28 to better contain the body exudates. Such containment flaps 56 are generally well known to those skilled in the art. For example, suitable constructions and arrangements for containment flaps 56 are described in U.S. Pat. No. 4,704,116 issued Nov. 3, 1987, to K. Enloe the disclosure of which is hereby incorporated by reference.

The disposable diaper 20 of the different aspects of the present invention may further include elastics at the waist edge 32 and side edges 30 of the absorbent chassis 28 of the diaper 20 to further prevent leakage of body exudates and support the absorbent chassis 28. For example, as representatively illustrated in FIGS. 1, 2 and 4, the diaper 20 of the present invention may include a pair of leg elastic members 54 which are connected to the laterally opposed side edges 30 of the absorbent chassis 28 in the crotch region 26 of the diaper 20 and a waist elastic member 58 which is connected to the waist edge 32 of the absorbent chassis 28 of the diaper 20. The leg elastics 54 and waist elastic 58 are generally adapted to fit about the legs and waist of a wearer in use to maintain a positive, contacting relationship with the wearer to effectively reduce or eliminate the leakage of body exudates from the diaper 20.

Materials suitable for use as the leg elastics 54 and waist elastic 58 are well known to those skilled in the art. Exemplary of such materials are sheets or strands or ribbons of a polymeric, elastomeric material which are adhered to the outer cover 42 in a stretched position, or which are attached to the outer cover 42 while the outer cover is pleated, such that elastic constrictive forces are imparted to the outer cover 42. The leg elastics may also include such materials as polyurethane, synthetic and natural rubber.

The prefastened, refastenable, disposable diaper 20 of the different embodiments of the present invention further includes at least one stretch panel 70 located in at least one of the waist regions 22 and 24 to provide a more comfortable, contouring fit about the wearer. The diaper 20 may include a stretch panel 70 disposed in both waist regions 22 and 24 and, desirably, the diaper includes a stretch panel 70 in at least the rear waist region 24. For example, as representatively illustrated in FIGS. 1–5, the diaper 20 includes a stretch panel 70 located on the body-facing surface 34 in the rear waist region 24 of the absorbent chassis 28. The illustrated stretch panel 70 generally defines a waist edge 72, a pair of laterally opposed outboard edges 74 which are located laterally beyond the side edges 30 of the absorbent chassis 28, and an inward edge 76 which is located longitudinally inward from the waist edge 72. As illustrated in FIG. 5, the stretch panel further defines a width 71 in the lateral direction 40 and a length 73 in the longitudinal direction 38.

The stretch panel 70 is configured to elongate in the lateral direction 40 at least about 30 percent and desirably at least about 50 percent to provide an improved fit and appearance of the diaper about the wearer by initially providing a conforming fit about the wearer and maintaining such fit throughout the use of such diaper. The stretch panel 70 is also configured such that the absorbent chassis 28 has the ability to expand, contract, and receive body exudates without adversely affecting the positioning of the stretch panel and the diaper about the waist of the wearer. Thus, with such a stretch panel 70, movements of the wearer may move the absorbent chassis 28 but do not adversely affect the overall positioning of the diaper on the wearer. Such improved fit results in reduced leakage from the waist and leg regions of the diaper and a more aesthetically pleasing appearance.

In a particular embodiment, the stretch panel 70 may be secured to the absorbent chassis 28 of the diaper 20 such that in an unstrained configuration the stretch panel 70 effectively contracts the waist region of the absorbent chassis 28 in the lateral direction 40. Desirably, the stretch panel 70 may be secured to the absorbent chassis 28 such that the width of the stretch panel 70 in the lateral direction 40 between the points at which it is attached to the absorbent chassis 28 is less than a fully extended width of the absorbent chassis 28. For example, the stretch panel 70 may be elongated and attached to the absorbent chassis 28 of the diaper 20 in an elastically contractible condition while the chassis of the diaper is in an uncontracted condition. Alternatively, the stretch panel 70 may be secured to the absorbent chassis 28 of the diaper when the absorbent chassis is in a tucked or pleated condition. The stretch panel 70 may otherwise include a latent elastic material along at least a portion of its width such that, after activation, the latent elastic material effectively contracts the waist region of the absorbent chassis 28.

In such a configuration, the stretch panel 70 is desirably secured to the absorbent chassis 28 of the diaper 20 such that, in an unstrained configuration, the absorbent chassis 28 of the diaper is gathered from about 3 to about 50 percent, more desirably from about 5 to about 30 percent, and most desirably from about 7 to about 20 percent. As a result, the portion of the stretch panel 70 between the side edges 30 of the absorbent chassis 28 may be capable of elongating in the lateral direction from a relaxed condition until the absorbent chassis is extended to its full width to provide the improved fit and containment. To provide even further extension, the absorbent chassis 28 may include materials which are capable of extension such as necked or elastic materials. As a result of it's elastic properties, the stretch panel 70 is able to snugly fit the wearer's body independent of the absorbent chassis 28 and any forces exerted on the chassis due to movements of the wearer and loading for improved performance.

As illustrated in the various embodiments of the present invention, the laterally outboard edges 74 of the stretch panel 70 extend beyond the side edges 30 of the absorbent chassis 28 of the diaper 20. The waist edge 72 of the stretch panel 70 is also generally coterminous with the end edge 32 of the chassis 28 of the diaper 20 in the respective waist region 22 or 24 in the illustrated embodiments. Alternatively, the waist edge 72 of the stretch panel 70 may extend longitudinally beyond the end edge 32 of the chassis 28 of the diaper 20, or the end edge 32 of the chassis 28 of the diaper 20 may extend longitudinally beyond the waist edge 72 of the stretch panel 70. In a particular embodiment, the waist edge 72 of the stretch panel 70 extends longitudinally beyond the end edge 32 of the absorbent chassis 28 to provide improved seals against the body of the wearer.

The stretch panel 70 also defines an inward edge 76 which extends longitudinally inward towards the crotch region 26 of the diaper 20. The inward edge 76 of the stretch panel 70 may be configured to remain at least partially unattached to the bodyside liner 44 or absorbent chassis 28 of the diaper 20 when in use to allow the absorbent chassis 28 to move and expand to receive and contain body exudates. Alternatively, in a particular embodiment, the inward edge 76 of the stretch panel 70 remains substantially fully attached to the absorbent chassis 28 to allow the absorbent chassis 28 to provide a close fit to the wearer's body for improved performance. The inward edge 76 of the stretch panel 70 may be linear. Alternatively, the inward edge 76 of the stretch panel 70 may be curvilinear, such as concave, to better fit the wearer. Desirably, if the inward edge 76 is curvilinear, the waist edge 72 may also be curvilinear such that consecutive stretch panels 70 for multiple articles nest within each other and can be provided from a continuous sheet of material. In such a configuration, the inward edge 76 of the first stretch panel corresponds to the waist edge 72 of the next stretch panel to improve manufacturing and reduce waste.

The longitudinal length 73 of the stretch panel 70 is generally sufficient to effectively distribute the fastening forces across a wide cross sectional area to provide improved fit without excessive irritation of the skin of the wearer. Desirably, the stretch panel 70 defines a longitudinal length 73 which is at least about 5 percent and more desirably from about 10 to about 30 percent of the longitudinal length 52 of the diaper 20. Lengths less than the above-specified ranges do not provide the improved fit and appearance of the article on the wearer and may result in excessive red marking. Whereas, lengths greater than the above specified ranges may extend too far into the crotch region 26 of the article such that the stretch panel 70 may interfere with the deposition of body exudates into the diaper article.

The stretch panel 70 extends laterally across the diaper 20 extending beyond the side edges 30 of the absorbent chassis 28. In particular, the stretch panel 70 defines a lateral width 71 that is greater than the width 50 of the absorbent chassis at the respective waist region to which the stretch panel 70 is attached to provide the improved fit and performance. As used herein, the width 50 of the absorbent chassis 28 refers to the distance between the outermost portions of the backsheet and/or topsheet layer in the lateral direction 40 at the desired lengthwise location along the diaper 20. In a particular embodiment, the stretch panel 70 defines a width 71 which is at least about 105 percent, desirably at least about 115 percent, and more desirably at least about 125 percent of the width 50 of the chassis of the diaper 20 at the respective waist region. For example, the stretch panel 70 may define a lateral width 71 of from about 105 to about 150 percent of the width 50 of the absorbent chassis 28 of the diaper 20 at the respective waist region. Widths less than the above-specified ranges do not provide the improved fit and appearance of the diaper 20 on the wearer.

The stretch panel 70 of the different embodiments of the present invention may be provided in a variety of ways. For example, the stretch panel 70 may be a single piece of material or a combination of individual pieces or panels of material attached to the diaper using conventional attachment means such as those described above. Desirably, the stretch panel 70 or at the least individual pieces or panels of the stretch panel 70 comprise elastic composite materials or non-stretchable materials which have been rendered elastically contractible by means known to those skilled in the art. It is also generally desirable that the stretch panel 70 be formed from materials which are substantially impermeable to liquids and which provide a more clothlike feeling. Such materials are capable of maintaining a close conforming fit while not irritating the skin of the wearer. Suitable elastomeric materials include SBL materials, NBL materials, elastomeric films, elastomeric foams, latent elastic materials and the like and combinations thereof.

In the embodiment illustrated in FIGS. 1–5, 6–10 and 13–15, the stretch panel 70 includes a single piece of elastomeric material. Such a single piece of material may be modified in any area or areas to provide the desired elastic properties. For example, in a particular embodiment, the elastic properties of portions of the stretch panel 70 may be modified by bonding the material at specific locations or zones to render such bonded areas less elastic than the unbonded areas. The effect the bonding has on the elastic properties of the material can depend upon several factors, including the area of the bonding or the bond point density.

In a particular embodiment wherein the stretch panel 70 includes an elastomeric material, it is desirable that the stretch panel 70 be capable of providing an elongation in the lateral direction 40 of at least about 5 percent, more desirably at least about 15 percent, and even more desirably at least about 30 percent when subjected to a tensile force load of about 80 grams in the lateral direction 40 per lineal centimeter of the sample measured in the longitudinal direction 38. Moreover, it is also desirable that the stretch panel 70 be capable of providing a tension range of from about 20 to about 400 grams, more desirably 20 from about 40 to about 275 grams, and even more desirably from about 60 to about 200 grams per lineal centimeter of the sample measured in the longitudinal direction 38 when subjected to an elongation of 30 percent in the lateral direction 40.

In another alternative configuration, the stretch panel 70 may be provided by a substantially non-elastomeric material, such as polymer films, woven fabrics, non-woven fabrics, or the like such as described above as being suitable for the outer cover 42 or bodyside liner 44. Such a stretch panel could be modified to render portions elastically contractible to provide the desired elastic properties to the stretch panel 70. For example, the stretch panel 70 may be made elastic or stretchable by means well known to those skilled in the art. For example, different portions of the stretch panel 70 may include a plurality of elastic strands which are elongated and adhesively attached in the lateral direction 40 to the respective portions of the stretch panel 70. Suitable elastic strands are known to those skilled in the art. For example, a suitable elastic strand may be composed of a 470 decitex LYCRA elastomer or a 620 decitex LYCRA elastomer commercially available from E. I. DuPont de Nemours Co., a business having offices located in Wilmington, Del., or other elastomers with suitable characteristics.

Alternatively, a piece of elastic material may be adhesively attached to the respective portions of the stretch panel 70 in an elongated condition to provide the desired stretchability. The piece of elastic material may include a SBL material, a NBL material, an elastomeric film, an elastomeric foam material, or the like as described above. In one embodiment, the piece of elastic material may be applied to the stretch panel in a pretensioned configuration. In another example, the elastic material may be latent, in which case the elastic material would initially have non-elastomeric properties, but would later be activated to impart elastomeric properties to the stretch panel by any of various means known to those skilled in the art. Suitable latent elastic materials are well known to those skilled in the art.

Alternatively, the stretch panel 70 may include two or more pieces or panels of material connected together, For example, as representatively illustrated in FIGS. 11–12, the stretch panel 70 may generally define a center bridge panel 100 which is flanked by and connected to a pair of laterally opposed side panels 102 along attachment zones 106. The side panels 102 are connected to and extend outward in a lateral direction 40 from the bridge panel 100 beyond the side edges 30 of the absorbent chassis 28 of the diaper 20. In use, the bridge panel 100 is generally configured to be located on the front or back abdominal regions of the wearer, while the side panels 102 are generally configured to be located on the side hips region of the wearer. In such a configuration, the particular location, size, and elastic nature of each panel of the stretch panel 70 is important to the performance of the stretch panel 70 in use.

On the majority of typical wearers of such absorbent articles and, in particular, on infants, the small or central portion of the wearer's back is generally concave (bowed inwards) or flat in shape and the front abdominal region of the wearer is generally convex or curved outwards. As a result, it has been difficult to maintain a tight seal between the absorbent article and the wearer in these areas. Depending upon whether the stretch panel 70 of the present invention is located in the front or the rear waist regions 22 and 24 of the diaper 20, the bridge panel 100 of the stretch panel 70 corresponds to the area of the stretch panel 70 which is intended to be in contact with either the small of the wearer's back or the outwardly curved front abdominal region when in use. The bridge panel 100 is configured to provide a conforming fit of the stretch panel 70 to these locations on the wearer.

As representatively illustrated in FIG. 12, the bridge panel 100 of the stretch panel 70 is typically centered about the longitudinal centerline of the diaper 20 and defines a width 101 which generally corresponds to the width of the small of the wearer's back or front abdominal region. For example, the width 101 of the bridge panel 100 of the stretch panel 70 may be from about 10 to about 100 percent and desirably from about 30 to about 70 percent of the width 50 of the absorbent chassis 28 of the article at the respective waist region. In a particular embodiment, the width 101 of the bridge panel 70 is at least about 10 percent, desirably at least about 25 percent, and more desirably at least about 40 percent of the width 50 of the absorbent chassis 28 of the article at the respective waist region. For example, the width 101 of the bridge panel 100 on a diaper article which is intended to be worn by a medium-sized infant weighing from about 16 to about 28 pounds may be from about 10 to about 15 centimeters. Width dimensions less than the above-specified ranges are not sufficient to extend along the entire width of the small of the wearer's back or the wearer's front abdominal region.

The side panels 102 of the stretch panel 70 are generally the areas of the stretch panel 70 which are intended to be in contact with the convex surface of the outer hip regions of the wearer when in use. As representatively illustrated in FIG. 12, the side panels 102 of the stretch panel 70 are attached to and laterally flank the bridge panel 100 of the stretch panel 70. The illustrated side panels 102 are also attached to and extend laterally beyond the side edges 30 of the absorbent chassis 28 of the article. Each of the side panels 102 defines a width 103 which generally corresponds to the width of the portions of the diaper article which are intended to be positioned on the hip regions of the wearer in use. For example, the width 103 of each side panel 102 may be from about 10 to about 70 percent and desirably from about 35 to about 50 percent of the width 50 of the absorbent chassis 28 of the article at the respective waist region to which the stretch panel 70 is attached.

In the embodiments illustrated in FIGS. 11 and 12, the side panels 102 of the stretch panel 70 also extend laterally inward from the side edges 30 of the absorbent chassis 28 to the bridge panel 100. The distance the side panels 102 extend inwardly will vary depending upon the desired width 101 of the bridge panel 100. In a particular embodiment wherein the diaper includes a pair of longitudinally extending containment flaps located between the side edges of the article, it is further desired that the side panels 102 of the stretch panel 70 extend laterally inwardly from the side edges 30 at least to the nearest containment flap for improved performance.

In such a configuration, the elastic nature or properties of each panel are designed such that the stretch panel 70 is capable of expanding and contracting with the movements of the wearer to enhance the fit of the article on the wearer. For example, the side panels 102 of the stretch panel 70 may be configured to be less elastic or stretchable than the bridge panel 100. Alternatively, the bridge panel 100 of the stretch panel 70 may be less stretchable than the side panels 102. Such arrangements will depend upon several factors including the general size and shape of the intended wearer, the intended loading of the article on the wearer, and the size, shape, and dimensions of the different panel sections of the fit panel.

In a preferred embodiment, the bridge panel 100 of the stretch panel 70 is elastomeric, and the side panels 102 of the stretch panel 70 are substantially non-elastomeric, such that the bridge panel 100 can stretch about the waist of the wearer to provide an optimum fit and seal, and such that the side panels do not stretch and thus do not interfere with the fit and gasketing properties of the leg elastics 54. For example, the bridge panel 100 and the side panels 102 may be configured such that, when lateral force is exerted on the stretch panel 70, the bridge panel elongates in the lateral direction, while the side panels do not elongate in the lateral direction. In such a configuration, the bridge panel 100 is configured to elongate in the lateral direction 40, and the side panels 102 are configured not to elongate in the lateral direction 40, when the diaper article is fit about the waist and hips of the wearer and fastened thereto. Specifically, the bridge panel 100 is configured to exert a force about the waist region of the wearer to provide a close-to-the-body fit and reliably maintain the diaper about the waist of the wearer. The elastic properties of the bridge panel 100 of the stretch panel 70 are also configured to distribute most of the forces exerted by the fasteners and any movements of the wearer such that such forces do not adversely affect the positioning and movement of the absorbent chassis 28 of the diaper 20. Further, the non-elastomeric properties of the side panels 102 are configured so as not to interfere with the fit and gasketing properties of the nearby leg elastics 54. To provide such properties in the stretch panel 70, the bridge panel is generally capable of being elongated in the lateral direction 40 from about 5 percent to about 200 percent, desirably from about 15 percent to about 150 percent, and more desirably from about 30 percent to about 90 percent from a relaxed condition.

The stretch panel 70 as representatively illustrated in FIGS. 11 and 12 can be provided in any suitable manner which provides the desired fit properties and performance. For example, the bridge panel 100 and side panels 102 may be provided by three individual pieces of material, some or all of which may be elastomeric, which are joined together along their side edges to provide the stretch panel 70. Suitable elastomeric materials include those described above as being suitable for a single piece stretch panel 70.

The stretch panel 70 of the different embodiments of the present invention may be attached to the absorbent chassis 28 of the diaper 20 in any suitable manner which provides the desired properties. For example, the stretch panel 70 may be attached to the absorbent chassis using adhesive, ultrasonic, thermal bonding techniques and the like or combinations thereof. As representatively illustrated in FIG. 4, the stretch panel 70 may be attached to the absorbent chassis of the diaper 20 along a lateral attachment zone 78 and a pair of opposed longitudinal attachment zones 79. In the illustrated embodiment, the lateral attachment zone 78 is generally located along or near the end edge 32 of the absorbent chassis 28 of the diaper 20 while the longitudinal attachment zones 79 are located along the side edges 30 of the absorbent chassis 28 in the respective waist region of the diaper 20. The lateral and longitudinal attachment zones 78 and 79, respectively, generally extend in the lateral and longitudinal directions 40 and 38, respectively, but may otherwise extend at angles from the lateral and longitudinal directions depending upon the configuration of the stretch panel 70 and the desired distribution of forces across the stretch panel. Such angled attachment zones can result in improved fit. As illustrated, the stretch panel 70 need not be attached to the absorbent chassis 28 of the diaper 20 along its entire width or length to allow additional freedom of movement for the absorbent chassis 28 relative to the stretch panel 70 for improved performance.

Further, the stretch panel 70 of the present invention may be attached to the absorbent chassis 28 of the diaper 20 in any location which provides the desired properties. For example, as representatively illustrated in FIGS. 1–12, the stretch panel 70 may be attached to the bodyfacing surface 34 of the bodyside liner 44 of the absorbent chassis 28 such that the stretch panel 70 contacts the wearer's skin. In such a configuration, as representatively illustrated in FIG. 4, the inward edge 76 of the stretch panel 70 may be unattached to the absorbent chassis 28 such that a pocket exists to contain body exudates. The illustrated pocket is defined by the inward edge 76, the lateral attachment zone 78 and the longitudinal attachment zones 79. Alternatively, the inward edge 76 of the stretch panel 70 may be substantially fully attached to the absorbent chassis 28.

As representatively illustrated in FIGS. 13–15, the stretch panel 70 may otherwise be attached to the garment facing surface 36 of the outer cover 42 of the absorbent chassis 28 such that the stretch panel 70 gives a more trim appearance to the diaper 20 during wear. In yet another embodiment, the stretch panel 70 may be sandwiched between the inner surfaces of both the bodyside liner 44 and the outer cover 42, both of which face the absorbent core 46.

The prefastened disposable diaper of the different aspects of the present invention further includes a prefastened, refastenable fastening system 60 for securing the diaper about the waist of the wearer. The fastening system 60 includes fasteners located on one of the waist regions 22 and 24 of the diaper 20 which are configured to releasably engage the opposite waist region of the diaper 20 to maintain the diaper about the waist of the wearer. The use of fasteners which are refastenable or releasably engageable allows for ease of securing and removing the diaper 20 from the waist of the wearer without undesirably soiling the wearer. The use of refastenable fasteners further readily allows for the inspection of the inside of the diaper 20 to determine if it has been soiled with the ability to refasten if it is not soiled.

The illustrated prefastened, refastenable fastening system 60 includes a pair of primary fasteners 62, one located on each laterally opposed side 74 of the stretch panel 70 in the rear waist region 24 of the diaper 20. In such a configuration, the primary fasteners 62 are refastenably engaged with the garment facing surface 36 of the absorbent chassis 28 in the front waist region 22 to provide the prefastened diaper 20. Alternatively, the primary fasteners 62 may be located on the front waist region 22 and may be configured to releasably engage the garment facing surface 36 in the rear waist region 24 of the absorbent chassis 28 to provide the prefastened diaper 20.

Desirably, the primary fasteners 62 are refastenably engaged directly with the garment facing surface 36 of the outer cover 42 of the absorbent chassis 28 of the diaper 20 to provide improved fit and ease of fastening. Alternatively, as representatively illustrated in FIGS. 1–3, the disposable diaper of the present invention may further include an attachment panel 66 located on the outer cover 42 in one of the waist regions 22 and 24 of the diaper 20. In such a configuration, the primary fasteners 62 are refastenably engaged with the attachment panel 66 to provide the prefastened diaper 20 and maintain the diaper 20 about the waist of the wearer. When the primary fasteners 62 are releasably engaged, the side edges 30 of the absorbent chassis 28 define leg openings which are configured to encircle the legs of the wearer and the waist regions 22 and 24 of the absorbent chassis 28 define a waist opening which is configured to encircle the waist of the wearer. In the illustrated embodiments, the attachment panel 66 is a single piece of material which extends substantially across the respective waist region of the diaper 20. Alternatively, the attachment panel 66 may include two separate panels located along the opposed side edges of the absorbent chassis 28 in one of the waist regions 22 and 24 of the diaper 20.

In the different aspects of the present invention, the primary fasteners 62 are refastenably engaged with the outer garment facing surface of the opposite waist region 22 and 24 of the diaper 20 before the diaper 20 is placed on the wearer to provide a prefastened, refastenable disposable diaper. In such a configuration, the prefastened diaper 20 can be pulled on or off over the legs and hips of the wearer. If the prefastened diaper 20 becomes soiled during use, the primary fasteners 62 can be disengaged to easily remove the diaper 20 from the waist of the wearer with reduced risk of undesirably soiling the clothes or legs of the wearer. The primary fasteners 62 can also be easily disengaged to inspect the diaper 20 for possible soiling or to first apply the product to the wearer if desired. Thus, the diaper 20 is configured to be pulled on or off over the hips of the wearer such as conventional training pants and can be readily applied or removed by disengaging the fasteners similar to conventional diaper articles. Moreover, the primary fasteners 62 can be repositioned if necessary after the prefastened diaper 20 has been pulled on over the legs and hips of the wearer to adjust the fit of the diaper to the wearer.

Suitable fasteners are well known to those skilled in the art and can include adhesive tape tab fasteners, hook and loop fasteners, mushroom fasteners, snaps, pins, belts and the like, and combinations thereof. For example, as representatively illustrated in FIGS. 1–3, the primary fasteners 62 may be hook type fasteners and the outer cover 42 or attachment panel 66 may be configured to function as a complimentary loop type fastener. Desirably, the primary fasteners 62 are hook type fasteners which are refastenably engageable directly with the outer cover 42. Such an arrangement provides the ability to vary the size of the waist opening in very small increments over a wide range to fit the waist of the wearer.

The fastening system 60 on the prefastened disposable diaper 20 of the present invention may also include at least one secondary fastener tab to provide improved securement of the diaper 20 about the waist of the wearer after the primary fasteners 62 have been releasably engaged. In particular, the secondary fastener is configured to further conform the waist regions 22 and 24 of the diaper 20 to the waist of the wearer. For example, as representatively illustrated in FIGS. 6–10, the diaper 20 of the present invention may include a pair of secondary fasteners 84 and 86. Alternatively, the diaper 20 may include a single secondary fastener.

In the illustrated embodiments, the secondary fasteners 84 and 86 are located within the laterally opposed sides 82 of the stretch panel 70 of the diaper 20. In use, the secondary fastener tabs 84 and 86 are configured to encircle the hips of the wearer and engage the garment facing surface 36 of the absorbent chassis 28 of the diaper 20. In the illustrated embodiments, the stretch panel 70 is located in the rear waist region 24 of the absorbent chassis 28. In such a configuration, the secondary fastener tabs 84 and 86 are configured to encircle the hips of the wearer and engage the garment facing surface 36 in the front waist region 22 to further conform the waist regions to the wearer. Alternatively, if the stretch panel 70 is located in the front waist region 22, the secondary fasteners 84 and 86 may be configured to releasably engage the garment facing surface 36 in the rear waist region 24 of the absorbent chassis 28 to further conform the waist regions to the wearer. The secondary fastener of the diaper 20 may also be provided in other alternative configurations known to those skilled in the art.

Desirably, the secondary fastener is releasably engageable directly with the garment-facing surface 36 of the outer cover 42 of the absorbent chassis 28 to provide improved ease of fastening. Alternatively, as described above and representatively illustrated in FIGS. 6–8, the diaper 20 of the present invention may further include an attachment panel 66 located on the outer cover 42 in one of the waist regions 22 and 24 of the diaper 20. In such a configuration, the secondary fastener may also be releasably engageable with the attachment panel 60 to further conform the diaper 20 to the waist of the wearer.

The use of at least one secondary fastener has been found to be particularly desirable when the primary fasteners 62 are releasably engaged with the respective waist region of the diaper 20 to provide a prefastened diaper which can be pulled on over the legs and hips of the wearer. In such a configuration, the waist opening of the diaper 20 when the primary fasteners 62 are engaged must be sufficient to allow the prefastened diaper to be pulled over the hips of the wearer. However, the circumference of the waist of the wearer is typically less than the circumference around the hips of the wearer. Thus, the waist opening of the prefastened diaper may not conform to the waist of the wearer which may undesirably result in leaks. In such a configuration, the secondary fastener of the diaper 20 of the present invention is configured to conform the waist regions of the diaper 20 to the wearer after the prefastened diaper is pulled on the wearer. Thus, the caregiver is not required to reposition the primary fasteners 62 to conform the waist regions 22 and 24 to the waist of the wearer. As a result, when the diaper 20 is to be removed from the wearer, the care giver may simply disengage the secondary fastener if necessary and pull the prefastened diaper down over the hips and legs of the wearer without having to reposition the primary fasteners 62.

In such configurations, the secondary fastener is intended to maintain the diaper 20 in a close conforming fit about the waist of the wearer to reduce the leakage of body exudates when in use. The primary fasteners 62 are intended to maintain the front and rear waist regions 22 and 24 connected in such a manner that the diaper 20 can be pulled on or off over the hips of the wearer after the secondary fastener or fasteners have been disengaged. The secondary fastener may also be selectively disengaged to facilitate inspection of the diaper 20 to determine if it has been soiled. The primary fasteners 62 can also provide a "childproofing function" by maintaining the diaper 20 at least partially secured about the waist of the wearer if the wearer disengages the secondary fastener.

The secondary fastener may be provided in a variety of ways. For example, as representatively illustrated in FIGS. 6–10, the stretch panel may include a pair of laterally directed perforations 80 on at least one laterally opposed side 82 of the stretch panel 70 provide at least one secondary fastener tab 84. The illustrated stretch panel 70 includes such perforations on both sides of the stretch panel 70 thereby providing a pair of secondary fastener tabs 84 and 86. The laterally directed perforations 80 may be either parallel or non-parallel. Further, the perforations 80 may by either straight or curvilinear. In a preferred embodiment, as representatively illustrated in FIGS. 6–10, the secondary fastener tab is provided by a pair of laterally directed, straight, parallel perforations 80 on at least one laterally opposed side 82 of the stretch panel 70.

The perforations 80 are configured such that, in use, the caregiver would tear the stretch panel 70 along the laterally directed perforations 80 to create at least one secondary fastener tab 84. The secondary fastener tab 84 defines both an outwardly directed, unattached, free end, and an inwardly directed end which remains attached to the stretch panel 70. In such a configuration, after the perforations 80 are torn, the free end of the secondary fastener tab may be elongated in the lateral direction 40 as representatively illustrated in FIGS. 6, 7 and 10.

The secondary fastener tab, by virtue of being created out of the stretch panel 70, may comprise the same fastener type as the primary fasteners 62 already located on the edges 74 of the stretch panel 70. For example, as illustrated, the perforations 80 may extend into the primary fasteners 62 such that, when torn, the secondary fastener tab includes a portion of the primary fastener 62. Alternatively, the stretch panel 70 may include at least one separate secondary fastener attached thereto.

Suitable fasteners for the secondary fastener are described above as being suitable for the primary fastener. For example, as representatively illustrated in FIGS. 6–7, the primary fasteners 62 and secondary fasteners 84 and 86 may be hook-type fasteners and the outer cover 42 or attachment panel 66 may be configured to function as a complimentary loop-type fastener. Desirably, the fasteners 62, 84, and 86 are hook-type fasteners which are releasably engageable directly with the outer cover 42. Such an arrangement provides the ability to vary the size of the waist opening in very small increments over a wide range to fit the waist of the wearer. The fasteners may have any shape and size which provides the desired fastening of the diaper 20 about the waist of the wearer.

Figure 9:
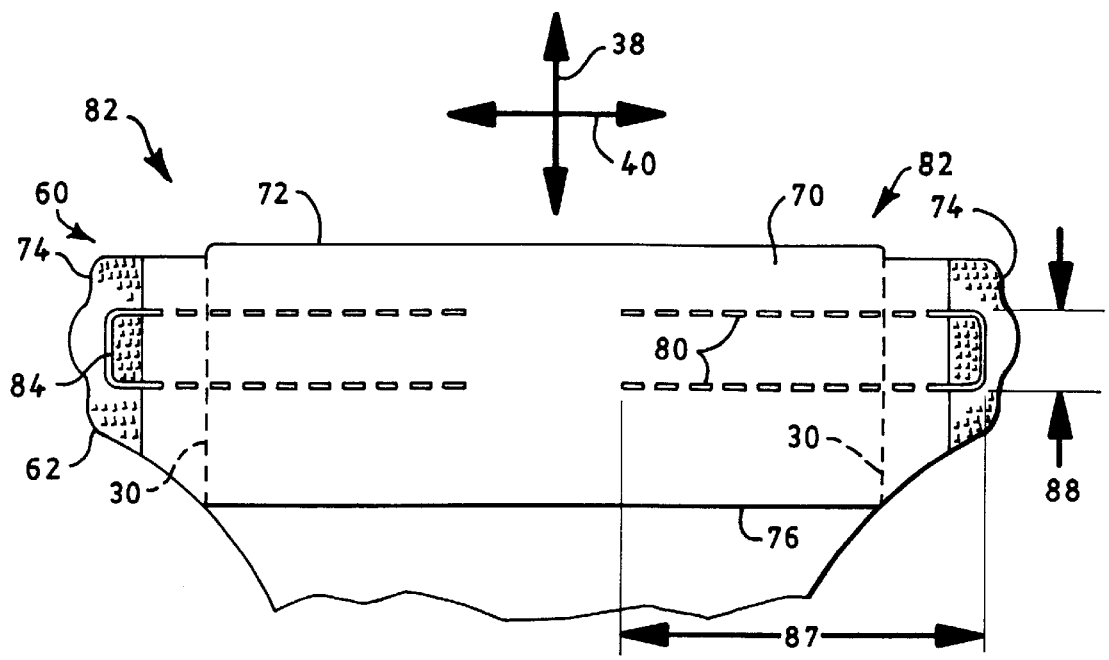
FIG. 9 representatively shows a top plan view of a portion of the prefastened disposable absorbent article of FIG. 6 in an unfastened, stretched, laid-flat condition with the surface of the article which contacts the wearer facing the viewer.
Figure 10:
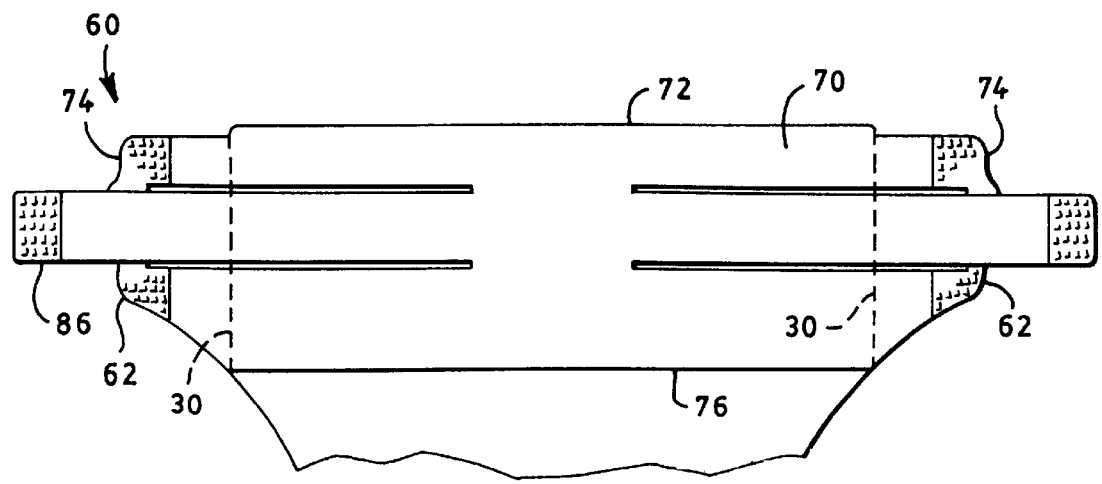
FIG. 10 representatively shows a top plan view of a portion of the prefastened disposable absorbent article of FIG. 6 in an unfastened, stretched, laid-flat condition with the surface of the article which contacts the clothing of the wearer facing the viewer.

The secondary fastener tab may define any length and width which provides the desired improved fastening and fit about the wearer. For example, the secondary fasteners tabs 84 and 86 in the illustrated embodiment, may each define a length 87 in the lateral direction 40 as illustrated in FIG. 9, which is at least about 5 percent, desirably at least about 20 percent, and more desirably at least about 35 percent of the lateral width 71 of the stretch panel 70. Further, the secondary fasteners 84 and 86 may each define a width 88 in the longitudinal direction 38 which is at least about 10 percent, desirably at least about 30 percent, and more desirably at least about 50 percent of the longitudinal length 73 of the stretch panel 70.

The prefastened diaper of the different aspects of the present invention may further include a pair of passive side bonds for improved reliability of maintaining the diaper 20 in the prefastened condition, particularly when it is being pulled on or off over the hips of the wearer. For example, as representatively illustrated in FIG. 13–15, the diaper 20 may include a pair of passive side bonds 90 which releasably connect an overlapped portion 92 of the rear waist region 24 and stretch panel 70 to the front waist region 22. In such a configuration, the passive side bonds 90 assist the fastening system 60 in maintaining the diaper 20 in a prefastened condition as the diaper 20 is pulled up or down over the hips of the wearer. Moreover, the passive side bonds 90 prevent movement and shifting of the waist regions 22 and 24 and stretch panel 70 relative to each other for improved fit and performance. The passive side bonds 90 also provide improved hip coverage and prevent rollover or folding of the side edges 30 and waist edges 32 of the absorbent chassis 28 of the prefastened diaper 20 as it is pulled over the wearer's hips. Such prevention of rollovers and foldovers can reduce the level of contact between the fasteners and the skin of the wearer which can desirably result in reduced skin irritation and redness.

As shown in the illustrated embodiments, the passive side bonds 90 are located inward of the primary fasteners 62 on the stretch panel 70 of the diaper 20. As used herein, the term "inward" refers to a distance in the lateral direction 40 towards the longitudinal centerline of the diaper 20 from the respective element. In such a configuration, the passive side bonds 90 connect and stabilize the overlapped portion 92 of the rear waist region 24 and stretch panel 70 inward of the primary fasteners 62 to the front waist region 22. Desirably, the passive side bonds 90 connect the overlapped portion 92 of the rear waist region 24 to the side edge 30 of the front waist region 22. For example, in the illustrated embodiment, the passive side bonds 90 bond a waist edge 72 and a portion of the inward edge 76 of the stretch panel 70 in the rear waist region 24 to the side edge 30 of the front waist region 22. In such a configuration, the passive bonds 90 assist in preventing the edges of the stretch panel 70 and absorbent chassis 28 from rolling over as the diaper 20 is pulled on.

As illustrated in FIG. 15, the overlapped portion 92 of the rear waist region 24 defines an overlap distance 94 which is the distance between the respective side edges 30 of the front and rear waist regions 22 and 24 when the diaper is prefastened. The overlap distance 94 is important to ensure that a good seal is provided around the legs and waist of the wearer. Moreover, the greater the overlap distance 94, the further inward the passive bonds 90 can be located which can provide improved reduction in the relative movement between the front and rear waist regions 22 and 24 and improved hip coverage during use. The larger overlap distance 94 is also desirable in the processing of the diaper 20 since the overlapped portion 92 is typically folded over and attached to the opposite waist region after the passive side bonds 90 are formed. To provide such improved fit and performance, it is desirable that the overlap distance 94 be at least about 2.0 centimeters and more desirably at least about 4.0 centimeters. As illustrated in FIG. 15, the passive bonds 90 may also be located on the opposite waist region a distance 96 inward form the side edge 30 of about 0.2 to about 2.5 centimeters for improved attachment and performance.

In a particular embodiment, the overlapped portions 92 of the rear waist region 24 are connected by the passive bonds 90 to the front waist region 22 along their edges 30 and 32 but remain unconnected by the passive bonds 90 to the front waist region 22 between the edges 30 and 32. In such an embodiment, the passive bonds 90 are not continuous along their length in the longitudinal direction 38. For example, as representatively illustrated in FIG. 15, the passive bonds 90 on each side of the rear waist region 24 may further define an unattached distance 98 in the longitudinal direction 38 between the respective bond points of at least about 1.0 centimeters and desirably at least about 2.0 centimeters. Such an arrangement is particularly useful when the fastening system 60 of the diaper 20 includes the secondary fastening tabs 84 and 86 described above such that the secondary fastener tabs 84 and 86 are allowed to freely be detached from the area created between the passive bonds 90.

As illustrated in FIG. 15, the passive side bonds 90 are located on the rear waist region 24 inward from the primary fastener 62 a distance 97 to prevent the relative movement or shifting between the front and rear waist regions 22 and 24 with respect to each other. In a particular embodiment, at least one of the bonds of each of the passive side bonds 90 is located on the rear waist region 24 a distance 97 inward from the primary fastener 62 of at least about 1.0 centimeters and desirably at least about 2.0 centimeters. When the distance 97 is less than the values set forth above, the front and rear waist regions 22 and 24 may undesirably shift with respect to each other during the application or use of the diaper 20. Such shifting of the respective waist regions 22 and 24 of the diaper 20 can adversely affect the fit of the diaper 20 on the wearer, which can undesirably lead to increased leakage.

In certain aspects of the invention, the location of the passive bonds 90 and the respective distance 97 and overlap distance 94 can be selectively varied to tailor the fit of the diaper 20 for different sized wearers. For example, the location of the bonds 90 may be varied during the manufacturing process such that the same process can produce prefastened diapers for use in conventional Step 3 or Step 4 sizes.

The passive side bonds 90 may connect the respective front and rear waist regions 22 and 24 in a facing relationship. For example, the passive side bonds 90 may connect the bodyfacing surface 34 of the absorbent chassis 28 in the rear waist region 24 to the garment facing surface 36 of the absorbent chassis 28 in the front waist region 22. Alternatively, the passive side bonds 90 may connect the bodyfacing surface 34 of the absorbent chassis 28 in the rear waist region 24 to the bodyfacing surface 34 of the absorbent chassis 28 in the front waist region 22. Such a configuration can lead to improved manufacturability. In such a configuration, the side edges 30 of the absorbent chassis 28 in the front waist region 22 may be folded over when the primary fasteners 62 are engaged.

The passive side bonds 90 can be provided by any type of bonding such as thermal, adhesive, ultrasonic, cohesive bonding and the like and combinations thereof as are well known to those skilled in the art. The passive side bonds 90 may otherwise be provided by suitable fasteners as are known to those skilled in the art and described above as being suitable for use as the primary fasteners 62. The passive side bonds 90 may be discrete point bonds, dashed lines, continuous lines, discontinuous lines and the like or combinations thereof. Moreover, the passive side bonds 90 may have any shape such as circular, square, triangular and the like. In a particular embodiment, the passive side bonds 90 are ultrasonic point bonds for improved manufacturing efficiency.

Methods of incorporating the passive side bonds 90 and making the prefastened diaper 20 of the different aspects of the present invention are known to those skilled in the art. For example, in addition to making the diaper by hand, one of such methods is described in copending U.S. patent application Ser. No. 09/100,911 entitled "METHOD OF MAKING PREFASTENED DISPOSABLE ABSORBENT ARTICLES" filed Jun. 19, 1998, in the name of Elsberg et al., the disclosure of which is hereby incorporated by reference.

The passive side bonds 90 are configured to assist the primary fasteners 62 in maintaining the diaper 20 in a prefastened configuration as the diaper 20 is pulled on and off over the hips of the wearer and during use. Thus, it is desirable that the passive side bonds 90 provide adequate shear strength for assisting the primary fasteners 62. In a particular embodiment, the passive side bonds 90 define a shear strength of at least about 50 grams and desirably at least about 100 grams. For example, the passive side bonds 90 may define a shear strength of from about 100 to about 4000 grams and desirably from about 500 to about 2000 grams. As used herein, the term "shear strength" refers to the value obtained when subjecting the side bonds to the Shear Strength Test described herein. Shear strength values less than those described above may not prevent the separation of the front and rear waist regions 22 and 24 from each other during the application and use of the diaper 20.

The passive side bonds 90 are also configured to be readily tearable such that the caregiver can easily pealingly remove the diaper 20 from the wearer after it has been soiled. Thus, it is desirable that the passive side bonds 90 define a relatively low peak peel strength such that the caregiver can readily disengage the fasteners 62, 84, and 86, break the passive side bonds 90, and separate the front and rear waist regions 22 and 24 to remove the diaper 20 from the waist of the wearer similar to conventional diapers which are not prefastened. For example, in a particular embodiment, the passive side bonds 90 define a peel strength of no more than about 1500 grams, desirably no more than about 1000 grams, and more desirably no more than about 800 grams. As used herein, the term "peel strength" refers to the value obtained when subjecting the side bonds to the Peel Strength Test described herein. Peel strength values greater than those described above may not be readily tearable and may undesirably result in tearing of other portions of the diaper 20. Desirably, the peel strength of the side bonds 90 is less than about 50 percent of the peel strength of the primary fasteners 62 and more desirably less than about 20 percent of the peel strength of the primary fasteners 62.

In another aspect, the present invention provides a package of the prefastened diapers described above. The package includes a container such as, for example, a plastic bag, and a plurality of prefastened disposable diapers. As described above, each prefastened diaper 20 includes at least one stretch panel 70 which is located in one of the waist regions 22 and 24 of the diaper 20. The stretch panel 70 is configured to elongate in the lateral direction 40 to provide an improved fit and appearance of the diaper about the wearer by initially providing a conforming fit about the wearer and maintaining such fit throughout the use of such article. Such a package provides diapers which can be pulled on over the legs of the wearer and which can be easily removed from the waist of the wearer after they have been soiled.

The different aspects of the present invention advantageously provide prefastened, refastenable, disposable absorbent articles, each of which may include the combination of at least one stretch panel, passive side bonds, and a prefastened, refastenable fastening system. The stretch panel is configured to elongate in the lateral direction to provide an improved fit and appearance of the diaper about the wearer by initially providing a conforming fit about the wearer and maintaining such fit throughout the use of such article. The stretch panel is also configured such that the absorbent chassis has the ability to expand, contract, and receive body exudates without adversely affecting the positioning of the stretch panel and the diaper about the waist of the wearer.

The primary fasteners are prefastened to refastenably engage the front and rear waist portions to allow the absorbent article to be pulled up or down over the hips of the wearer such as conventional training pants. Moreover, the primary fasteners can be used to refastenably engage and adjust the front and rear waist regions of the absorbent article to maintain the absorbent article about the waist of the wearer after the article has been pulled on in a similar manner to conventional diapers. Further, the fastening system may include at least one secondary fastener to provide improved securement of the diaper about the waist of the wearer after the primary fasteners have been releasably engaged. The passive side bonds assist the fastening system in maintaining the article in a prefastened condition as the article is pulled up or down over the hips of the wearer. Moreover, the passive side bonds prevent movement and shifting of the waist portions relative to each other for improved manufacturability, fit and performance. The passive side bonds also prevent the rollover or folding in of the side and waist edges of the prefastened absorbent article as it is pulled over the wearer's hips.

As a result, the prefastened absorbent articles of the present invention are designed to conform to the body of the wearer to effectively contain bodily exudates while still being capable of being reliably pulled up or down over the hips of the wearer to assist in the toilet training of the wearer. Moreover, similar to conventional diapers, the absorbent articles of the present invention can advantageously be applied to and removed from the wearer with relative ease and cleanliness.

Peel Strength Test

This test method is designed to quantify, in grams, the peak strength of the ultrasonic point bonds holding the front waist region of the absorbent article to the rear waist region. The direction of removal (peel), in this application, is that direction in which the fastener material would generally be removed from a substrate when the product is in use. This direction is generally perpendicular to a longitudinal centerline of the product.

Equipment
1. Tensile tester capable of obtaining a peak load and equipped with an appropriate load cell. A suitable tensile testing system is a Sintech Tensile Tester, commercially available from MTS Sintech, Research Triangle Park, North Carolina, under the trade designation Instron Model 4201 Tensile Tester with Sintech QAD (Quality Assurance Department) Software.
2. Software commercially obtained from MTS Sintech under the trade designation Sintech Testworks™.
3. Pnuematic-action grips commercially available from Instron Corporation, Canton, Mass., under the trade designation "Instron Model 2712-004."
4. 1 by 4 inch grip faces, serrated, commercially available from Instron Corporation, Canton, Mass.
5. Test facility having a temperature of 23±1° C., and a relative humidity of 50±2 percent.

Test Procedure
1. A sample to be tested is conditioned in the test facility for at least 4 hours prior to testing.
2. The load cell is calibrated and the software loaded.
3. The grips are installed on the tensile tester with the jaws closed.
4. The test condition for the tensile tester are set as follows:

| | |
|---|---|
| Crosshead speed: | 500 millimeters/minutes |
| Full-scale load: | 5 kilograms |
| Threshold: | 5 percent |
| Fail criterion: | 95 percent |
| Gage length: | 50 millimeters |

5. The weight of the clamp is tared out.
6. The primary fastener tab of the fastening element on the rear waist region of the article is inserted into the upper jaw such that the edge of the grip face is flush with the inner edge of the hook material.
7. The front waist region of the article is inserted into the lower jaw such that the inner surface of the rear waist region and the outer surface of the front waist region form a 180° angle. The lower jaw is closed.
8. The crosshead is started in motion.
9. The peak load of failure is recorded. It is intended that the mode of failure is that the rear waist region of the diaper separates from the front waist region of the diaper. Results are rejected if the place of failure is any location other than the ultrasonic point bonds.

Shear Strength Test

This test method is designed to quantify, in grams, the peak dynamic shear strength of the ultrasonic point bonds holding the front waist region of the absorbent article to the rear waist region. The direction of force in this application is generally perpendicular to the longitudinal centerline of the product.

Equipment
1. Tensile tester capable of obtaining a peak load and equipped with an appropriate load cell. A suitable tensile testing system is a Sintech Tensile Tester, commercially available from MTS Sintech, Research Triangle Park, North Carolina, under the trade designation Instron Model 4201 Tensile Tester with Sintech QAD (Quality Assurance Department) Software.
2. Software commercially obtained from MTS Sintech under the trade designation Sintech Testworks™.
3. Pnuematic-action grips commercially available from Instron Corporation, Canton, Mass., under the trade designation "Instron Model 2712-004."
4. 1 by 4 inch grip faces, serrated, commercially available from Instron Corporation, Canton, Mass.
5. Test facility having a temperature of 23±1° C., and a relative humidity of 50±2 percent.

Test Procedure
1. A sample to be tested is conditioned in the test facility for at least 4 hours prior to testing.
2. The load cell is calibrated and the software loaded.
3. The grips are installed on the tensile tester with the jaws closed.
4. The test condition for the tensile tester are set as follows:

| | |
|---|---|
| Crosshead speed: | 500 millimeters/minutes |
| Full-scale load: | 5 kilograms |
| Threshold: | 5 percent |
| Fail criterion: | 95 percent |
| Gage length: | 50 millimeters |

5. The weight of the clamp is tared out.
6. The primary fastener tab of the fastening element on the rear waist region of the article is inserted into the upper jaw such that the edge of the grip face is flush with the inner edge of the hook material.

7. The front waist region of the article is inserted into the lower jaw such that the inner surface of the rear waist region and the inner surface of the front waist region are facing the same direction and are parallel to one another. The lower jaw is closed.
8. The crosshead is started in motion.
9. The peak load of failure is recorded. It is intended that the mode of failure is that the rear waist region of the article separates from the front waist region of the article. Results are rejected if the place of failure is any location other than the ultrasonic point bonds.

Having thus described the invention in rather full detail, it will be readily apparent to a person of ordinary skill that various changes and modifications can be made without departing from the spirit of the invention. All of such changes and modifications are contemplated as being within the scope of the present invention as defined by the subjoined claims.

We claim:

1. A prefastened disposable absorbent article comprising an absorbent chassis which defines a front waist region, a rear waist region, a crotch region which extends between and connects said waist regions, a pair of longitudinally opposed end edges, and a pair of laterally opposed side edges, said absorbent article further comprising:
   a) at least one stretch panel which is located in one of said waist regions of said absorbent chassis and which defines a waist edge, a pair of laterally opposed outboard edges which are located laterally beyond said side edges of said absorbent chassis, and an inward edge which is located longitudinally inward from said waist edge, wherein said stretch panel is designed to elongate in a lateral direction at least about 30 percent to provide a conforming fit about a wearer's waist;
   b) a pair of primary fasteners which are located on said laterally opposed outboard edges of said stretch panel and which are releasably prefastened to an opposite waist region of said absorbent chassis to releasably engage said front waist region to said rear waist region to provide said prefastened disposable absorbent article; and
   c) a pair of passive side bonds which are located laterally inward of said primary fasteners on said one waist region and which releasably connect an overlapped portion of said one waist region to said opposite waist region to assist in maintaining said prefastened absorbent article in a prefastened condition.

2. The prefastened absorbent article of claim 1 wherein said passive side bonds releasably connect said overlapped portion of said one waist region to said side edges in said opposite waist region to assist in maintaining said prefastened absorbent article in said prefastened condition.

3. The prefastened absorbent article of claim 1 wherein said passive side bonds are located on said one waist region laterally inward from said primary fasteners a distance of at least about 1.0 centimeter.

4. The prefastened absorbent article of claim 1 wherein said overlapped portion of said one waist region defines an overlap distance of at least about 2.0 centimeters.

5. The prefastened absorbent article of claim 1 wherein said passive side bonds define a peel strength of no more than about 1500 grams.

6. The prefastened absorbent article of claim 1 wherein said passive side bonds connect a body facing surface of said absorbent article in said one waist region to a garment facing surface of said absorbent article in said opposite waist region.

7. The prefastened absorbent article of claim 1 wherein said passive side bonds connect a body facing surface of said absorbent article in said one waist region to a body facing surface of said absorbent article in said opposite waist region.

8. The prefastened absorbent article of claim 1 wherein said stretch panel comprises a latent elastic material.

9. The prefastened absorbent article of claim 1 wherein said stretch panel is designed to elongate in a lateral direction at least about 50 percent to assist in positioning said prefastened disposable absorbent article about a wearer's waist.

10. The prefastened absorbent article of claim 1 wherein said primary fasteners are hook and loop type fasteners.

11. The prefastened absorbent article of claim 1 wherein said stretch panel is attached to a body facing surface of said absorbent article.

12. The prefastened absorbent article of claim 1 wherein said absorbent chassis includes an outer cover and a bodyside liner and wherein said stretch panel is incorporated between said outer cover and said bodyside liner.

13. The prefastened absorbent article of claim 1 wherein said stretch panel is attached to a garment facing surface of said absorbent article.

14. The prefastened absorbent article of claim 1 wherein said inward edge of said stretch panel is substantially fully attached to said absorbent chassis.

15. The prefastened absorbent article of claim 1 wherein said passive side bonds include at least one point bond.

16. The prefastened absorbent article of claim 15 wherein said point bond is an ultrasonic point bond.

17. The prefastened absorbent article of claim 1 wherein said stretch panel is perforated along a pair of laterally directed lines on at least one of two laterally opposed sides of said stretch panel to provide at least one secondary fastener tab, said secondary fastener tab being configured to releasably engage said opposite waist region to further conform said waist region to a wearer's body after said prefastened disposable absorbent article is pulled on over a wearer's hips.

18. The prefastened absorbent article of claim 17 wherein said at least one secondary fasteners tab defines a length in a lateral direction which is at least about 10 percent of a total lateral width of said stretch panel.

19. The prefastened absorbent article of claim 17 wherein both said primary fasteners and said at least one secondary fastener tab are hook and loop type fasteners.

20. A prefastened disposable absorbent article comprising an absorbent chassis which defines a front waist region, a rear waist region, a crotch region which extends between and connects said waist regions, a pair of longitudinally opposed end edges, and a pair of laterally opposed side edges, and at least one stretch panel which defines a waist edge which is superposed adjacent said end edge of said absorbent chassis in one of said waist regions, a pair of laterally opposed outboard edges which are located laterally beyond said side edges of said absorbent chassis, and an inward edge which is located longitudinally inward from said waist edge, said stretch panel comprising
   a) a center bridge panel;
   b) a pair of laterally opposed side panels which are connected to opposed lateral edges of said bridge panel and which extend laterally beyond said side edges of said absorbent chassis, wherein said stretch panel is designed to elongate in a lateral direction at least about 30 percent to provide a conforming fit about a wearer's waist;

c) a pair of primary fasteners which are located on said laterally opposed outboard edges of said stretch panel and which are releasably prefastened to an opposite waist region of said absorbent chassis to releasably engage said front waist region to said rear waist region to provide said prefastened disposable absorbent article; and d) a pair of passive side bonds which are located laterally inward of said primary fasteners on said one waist region and which releasably connect an overlapped portion of said one waist region to said opposite waist region to assist in maintaining said prefastened absorbent article in a prefastened condition.

21. The prefastened absorbent article of claim 20 wherein said bridge panel defines a bridge panel width in a lateral direction which is at least about 10 percent of a width of said absorbent chassis.

22. The prefastened absorbent article of claim 20 wherein said primary fasteners are hook and loop type fasteners.

23. The prefastened absorbent article of claim 20 wherein said stretch panel is attached to a body facing surface of said absorbent article.

24. The prefastened absorbent article of claim 20 wherein said absorbent chassis includes an outer cover and a bodyside liner and wherein said stretch panel is incorporated between said outer cover and said bodyside liner.

25. The prefastened absorbent article of claim 20 wherein said stretch panel is attached to a garment facing surface of said absorbent article.

26. The prefastened absorbent article of claim 20 wherein said inward edge of said stretch panel is substantially fully attached to said absorbent chassis.

27. The prefastened absorbent article of claim 20 wherein said side panels of said stretch panel are substantially non-elastomeric.

28. The prefastened absorbent article of claim 27 wherein said bridge panel defines a bridge panel width in a lateral direction which is about equal to a width of said absorbent chassis, such that said bridge panel provides stretch in said one waist region and said side panels remain substantially non-elastomeric beyond said laterally opposed side edges of said absorbent chassis.

29. The prefastened absorbent article of claim 20 wherein said stretch panel is perforated along a pair of laterally directed lines on at least one of two laterally opposed sides of said stretch panel to provide at least one secondary fastener tab, said secondary fastener tab being configured to releasably engage said opposite waist region to further conform said waist regions to a wearer's body after said prefastened disposable absorbent article is pulled on over a wearer's hips.

30. The prefastened absorbent article of claim 29 wherein said at least one secondary fastener tab defines a length in a lateral direction which is at least about 10 percent of a total lateral width of said stretch panel.

31. The prefastened absorbent article of claim 29 wherein both said primary fasteners and said at least one secondary fastener tab are hook and loop type fasteners.

32. A prefastened disposable absorbent article comprising an absorbent chassis which defines a front waist region, a rear waist region, a crotch region which extends between and connects said waist regions, a pair of longitudinally opposed end edges, and a pair of laterally opposed side edges, said absorbent article further comprising:

a) a stretch panel located in each of said waist regions of said absorbent chassis, said stretch panel defining a waist edge, a pair of laterally opposed outboard edges which are located laterally beyond said side edges of said absorbent chassis, and an inward edge which is located longitudinally inward from said waist edge, wherein said stretch panel is designed to elongate in a lateral direction at least about 30 percent to provide a conforming fit about a wearer's waist; and b) a pair of primary fasteners which are located on said laterally opposed outboard edges of said stretch panel and which are releasably prefastened to an opposite waist region of said absorbent chassis to releasably engage said front waist region to said rear waist region to provide said prefastened disposable absorbent article.

33. A prefastened disposable absorbent article comprising an absorbent chassis which defines a front waist region, a rear waist region, a crotch region which extends between and connects said waist regions, a pair of longitudinally opposed end edges, and a pair of laterally opposed side edges, said absorbent article further comprising:

a) at least one stretch panel comprising a latent elastic material, where said stretch panel is located in one of said waist regions of said absorbent chassis and which defines a waist edge, a pair of laterally opposed outboard edges which are located laterally beyond said side edges of said absorbent chassis, and an inward edge which is located longitudinally inward from said waist edge, wherein said stretch panel is designed to elongate in a lateral direction at least about 30 percent to provide a conforming fit about a wearer's waist; and b) a pair of primary fasteners which are located on said laterally opposed outboard edges of said stretch panel and which are releasably prefastened to an opposite waist region of said absorbent chassis to releasably engage said front waist region to said rear waist region to provide said prefastened disposable absorbent article.

34. A prefastened disposable absorbent article comprising an absorbent chassis which defines a front waist region, a rear waist region, a crotch region which extends between and connects said waist regions, a pair of longitudinally opposed end edges, and a pair of laterally opposed side edges, said absorbent article further comprising:

a) at least one stretch panel which is located in one of said waist regions of said absorbent chassis and which defines a waist edge a pair of laterally opposed outboard edges which are located laterally beyond said side edges of said absorbent chassis, and an inward edge which is located longitudinally inward from said waist edge, wherein said stretch panel is designed to elongate in a lateral direction at least about 30 percent to provide a conforming fit about a wearer's waist;

b) a pair of primary fasteners which are located on said laterally opposed outboard edges of said stretch panel and which are releasably prefastened to an opposite waist region of said absorbent chassis to releasably engage said front waist region to said rear waist region to provide said prefastened disposable absorbent article; and wherein said stretch panel is perforated along a pair of laterally directed lines on at least one of two laterally opposed sides of said stretch panel to provide at least one secondary fastener tab, said secondary fastener tab being configured to releasably engage said opposite waist region to further conform said waist regions to a wearer's body after said prefastened disposable absorbent article is pulled on over a wearer's hips.

35. The prefastened absorbent article of claim 34 wherein said secondary fastener tab defines a length in a lateral direction which is at least about 5 percent of a total lateral width of said stretch panel.

36. The prefastened absorbent article of claim 34 wherein both said primary fasteners and said at least one secondary fastener tab are hook and loop type fasteners.

37. A package of prefastened disposable absorbent articles comprising a container and a plurality of said prefastened disposable absorbent articles, each of which comprise an absorbent chassis which defines a front waist region, a rear waist region, a crotch region which extends between and connects said waist regions, a pair of longitudinally opposed end edges, and a pair of laterally opposed side edges, each of said absorbent articles further comprising:
   a) at least one stretch panel which is located on one of said waist regions of said absorbent chassis and which defines a waist edge, a pair of laterally opposed outboard edges which are located laterally beyond said side edges of said absorbent chassis, and an inward edge which is located longitudinally inward from said waist edge, wherein said stretch panel is configured to provide a conforming fit about a wearer's waist;
   b) a pair of primary fasteners which are located on said laterally opposed outboard edges of said stretch panel and which are releasably prefastened to an opposite waist region of said absorbent chassis to releasably engage said front waist region to said rear waist region to provide said prefastened disposable absorbent article; and
   c) a pair of passive side bonds which are located inward of said primary fasteners on said one waist region and which releasably connect an overlapped portion of said one waist region to said opposite waist region to assist in maintaining said prefastened absorbent article in a prefastened condition.

38. A package of prefastened disposable absorbent articles comprising a container and a plurality of said prefastened disposable absorbent articles, each of which comprise an absorbent chassis which defines a front waist region, a rear waist region, a crotch region which extends between and connects said waist regions, a pair of longitudinally opposed end edges, and a pair of laterally opposed side edges, each of said absorbent articles further comprising:
   a) at least one stretch panel which is located on one of said waist regions of said absorbent chassis and which defines a waist edge, a pair of laterally opposed outboard edges which are located laterally beyond said side edges of said absorbent chassis, and an inward edge which is located longitudinally inward from said waist edge, wherein said stretch panel comprises a center bridge panel and a pair of laterally opposed side panels which are connected to opposed lateral edges of said bridge panel and which extend laterally beyond said side edges of said absorbent chassis, and wherein said stretch panel is configured to provide a conforming fit about a wearer's waist; and
   b) a pair of primary fasteners which are located on said laterally opposed outboard edges of said stretch panel and which are releasably prefastened to an opposite waist region of said absorbent chassis to releasably engage said front waist region to said rear waist region to provide said prefastened disposable absorbent article.

39. A package of prefastened disposable absorbent articles comprising a container and a plurality of said prefastened disposable absorbent articles, each of which comprise an absorbent chassis which defines a front waist region, a rear waist region, a crotch region which extends between and connects said waist regions, a pair of longitudinally opposed end edges, and a pair of laterally opposed side edges, each of said absorbent articles further comprising:
   a) at least one stretch panel which is located on one of said waist regions of said absorbent chassis and which defines a waist edge, a pair of laterally opposed outboard edges which are located laterally beyond said side edges of said absorbent chassis, and an inward edge which is located longitudinally inward from said waist edge, wherein said stretch panel is configured to provide a conforming fit about a wearer's waist;
   b) a pair of primary fasteners which are located on said laterally opposed outboard edges of said stretch panel and which are releasably prefastened to an opposite waist region of said absorbent chassis to releasably engage said front waist region to said rear waist region to provide said prefastened disposable absorbent article; and
wherein said stretch panel of said absorbent articles is perforated along a pair of laterally directed lines on at least one of two laterally opposed sides of said stretch panel to provide at least one secondary fastener tab, said secondary fastener tab being configured to releasably engage said opposite waist region to further conform said waist regions to a wearer's body after said prefastened disposable absorbent article is pulled on over a wearer's hips.

* * * * *